US007674480B2

(12) United States Patent
Fleshner-Barak et al.

(10) Patent No.: US 7,674,480 B2
(45) Date of Patent: *Mar. 9, 2010

(54) RAPIDLY EXPANDING COMPOSITION FOR GASTRIC RETENTION AND CONTROLLED RELEASE OF THERAPEUTIC AGENTS, AND DOSAGE FORMS INCLUDING THE COMPOSITION

(75) Inventors: Moshe Fleshner-Barak, Petach Tikva (IL); E. Itzhak Lerner, Petach Tikva (IL); Vered Rosenberger, Jerusalem (IL); Mazal Dahan, Jerusalem (IL); Yisrael Makov, Carmei Yosef (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 1135 days.

This patent is subject to a terminal disclaimer.

(21) Appl. No.: 09/887,204

(22) Filed: Jun. 22, 2001

(65) Prior Publication Data
US 2004/0234608 A1 Nov. 25, 2004

Related U.S. Application Data

(60) Provisional application No. 60/213,832, filed on Jun. 23, 2000, provisional application No. 60/217,110, filed on Jul. 10, 2000, provisional application No. 60/223,212, filed on Aug. 4, 2000.

(51) Int. Cl.
*A61K 9/14* (2006.01)
*A61K 9/16* (2006.01)
(52) U.S. Cl. .................. 424/488; 424/489; 424/486; 424/490
(58) Field of Classification Search .......... 424/484, 424/486, 473, 468, 433, 490, 846, 488; 514/76, 514/283, 89
See application file for complete search history.

(56) References Cited

U.S. PATENT DOCUMENTS

| | | | |
|---|---|---|---|
| 2,996,431 A | 8/1961 | Barry | |
| 3,139,383 A | 6/1964 | Neville | |
| 3,995,058 A | 11/1976 | Hammond et al. | |
| 4,140,755 A | 2/1979 | Sheth et al. | |
| 4,167,558 A | 9/1979 | Sheth et al. | |
| 4,190,672 A | 2/1980 | Fahn | |
| 4,326,525 A * | 4/1982 | Swanson et al. | 424/433 |
| 4,434,153 A | 2/1984 | Urquhart et al. | |
| 4,557,925 A | 12/1985 | Lindahl et al. | |
| 4,642,233 A | 2/1987 | Urquhart et al. | |
| 4,704,285 A | 11/1987 | Alderman | |
| 4,705,651 A | 11/1987 | Staibano | |
| 4,717,713 A | 1/1988 | Zatz et al. | |
| 4,721,613 A | 1/1988 | Urquhart et al. | |
| 4,752,470 A | 6/1988 | Mehta | |
| 4,756,911 A | 7/1988 | Drost et al. | |
| 4,758,436 A | 7/1988 | Caldwell et al. | |
| 4,764,380 A | 8/1988 | Urquhart et al. | |
| 4,767,627 A | 8/1988 | Caldwell et al. | |
| 4,853,229 A | 8/1989 | Theeuwes | |
| 4,919,938 A | 4/1990 | Lovegrove et al. | |
| 4,983,398 A | 1/1991 | Gaylord et al. | |
| 4,983,400 A | 1/1991 | Dempski et al. | |
| 5,007,790 A | 4/1991 | Shell | |
| 5,051,262 A | 9/1991 | Panoz et al. | |
| 5,198,229 A | 3/1993 | Wong et al. | |
| 5,232,704 A | 8/1993 | Franz et al. | |
| 5,443,843 A | 8/1995 | Curatolo et al. | |
| 5,560,933 A | 10/1996 | Soon-Shiong et al. | |
| 5,599,534 A | 2/1997 | Himmelstein et al. | |
| 5,603,955 A | 2/1997 | Gehrke et al. | |
| 5,780,057 A | 7/1998 | Conte et al. | |
| 5,837,284 A | 11/1998 | Mehta et al. | |
| 5,840,756 A | 11/1998 | Cohen et al. | |
| 5,874,090 A * | 2/1999 | Baker et al. | 424/400 |
| 5,958,443 A | 9/1999 | Viegas et al. | |
| 5,958,446 A | 9/1999 | Miranda et al. | |
| 5,972,389 A | 10/1999 | Shell et al. | |
| 5,989,589 A * | 11/1999 | Cartilier et al. | 424/465 |
| 6,120,803 A | 9/2000 | Wong et al. | |

(Continued)

FOREIGN PATENT DOCUMENTS

EP 0 761 209 3/1997

(Continued)

OTHER PUBLICATIONS

Hwang, Sung-Joo; Park, Haesun; Park, Kinam, "Gastric Retentive Drug-Delivery Systems", Critical Reviews in Therapeutic Drug Carrier Systems, 1998, vol. 15, Issue 3, pp. 243-284.

(Continued)

Primary Examiner—Blessing M Fubara
(74) Attorney, Agent, or Firm—Kenyon & Kenyon LLP

(57) ABSTRACT

The present invention provides a pharmaceutical composition for use in a dosage form for oral administration to a patient. The composition expands upon contact with gastric fluid and promotes retention of the dosage form in the patient's stomach for a prolonged period of time. The present invention further provides pharmaceutical dosage forms containing an active ingredient, and the pharmaceutical composition. The forms are adapted for immediate or controlled release of the active ingredient. The dosage forms may be used advantageously in the treatment of Parkinson's disease with levodopa and hyperactivity and attention deficit disorder with methylphenidate.

24 Claims, 1 Drawing Sheet

U.S. PATENT DOCUMENTS

| | | | |
|---|---|---|---|
| 6,143,326 | A | 11/2000 | Möckel et al. |
| 6,207,197 | B1 | 3/2001 | Illum et al. |
| 6,210,705 | B1 | 4/2001 | Mantelle et al. |
| 6,261,601 | B1 | 7/2001 | Talwar et al. |
| 6,271,278 | B1 | 8/2001 | Park et al. |
| 6,322,819 | B1 * | 11/2001 | Burnside et al. ............ 424/494 |
| 6,340,475 | B2 | 1/2002 | Shell et al. |
| 6,340,476 | B1 | 1/2002 | Midha et al. |
| 6,342,249 | B1 * | 1/2002 | Wong et al. ................. 424/473 |
| 6,344,215 | B1 | 2/2002 | Bettman et al. |
| 6,348,211 | B1 | 2/2002 | Mantelle et al. |
| 6,352,721 | B1 | 3/2002 | Faour |
| 6,368,626 | B1 | 4/2002 | Bhatt et al. |
| 6,419,960 | B1 | 7/2002 | Krishnamurthy et al. |
| 6,476,006 | B2 * | 11/2002 | Flashner-Barak et al. ..... 514/76 |
| 6,589,549 | B2 | 7/2003 | Shih et al. |
| 6,635,284 | B2 | 10/2003 | Mehta et al. |
| 6,673,367 | B1 | 1/2004 | Goldenheim et al. |
| 6,919,373 | B1 | 7/2005 | Lam et al. |
| 6,930,129 | B2 | 8/2005 | Lam et al. |
| 7,083,808 | B2 | 8/2006 | Goldenheim et al. |
| 2002/0006443 | A1 * | 1/2002 | Curatolo et al. ............ 424/486 |
| 2002/0035357 | A1 | 3/2002 | Faour et al. |
| 2002/0044960 | A1 | 4/2002 | Cherukuri |
| 2002/0044962 | A1 | 4/2002 | Cherukuri et al. |
| 2002/0136744 | A1 | 9/2002 | McGlynn et al. |
| 2002/0147208 | A1 * | 10/2002 | Fleshner-Barak et al. ... 514/283 |
| 2003/0158154 | A1 * | 8/2003 | Fleshner-Barak ............ 514/89 |
| 2003/0203878 | A1 * | 10/2003 | Flashner-Barak et al. ..... 514/89 |

FOREIGN PATENT DOCUMENTS

| | | |
|---|---|---|
| JP | H4-346919 | 12/1992 |
| WO | WO 92/09307 | 6/1992 |
| WO | WO 96/29055 | 9/1996 |
| WO | WO 98/11879 | 3/1998 |
| WO | WO 99/04764 | 2/1999 |
| WO | WO 99/32151 | 7/1999 |
| WO | WO 05/042101 | 5/2005 |

OTHER PUBLICATIONS

Chen, Jun; Park Kinam, "Synthesis and characterization of superporous hydrogel composites", Journal of Controlled Release 65, 2000, pp. 73-82.

The United States Pharmacopeia and The National Formulary, Jan. 1, 2000, 24/ 19, p. 2235 (1999).

Chen, Jun; Blevins, William E.; Park, Haesun; Park, Kinam, "Gastric retention properties of superporous hydrogel composites", Journal of Controlled Release 64, 2000, pp. 39-51.

US 6,034,101, 03/2000, Gupta et al. (withdrawn)

* cited by examiner

RAPIDLY EXPANDING COMPOSITION FOR GASTRIC RETENTION AND CONTROLLED RELEASE OF THERAPEUTIC AGENTS, AND DOSAGE FORMS INCLUDING THE COMPOSITION

CROSS-REFERENCE TO RELATED APPLICATIONS

This invention claims the benefit under 35 U.S.C. 119(e) of provisional applications Ser. No. 60/213,832, filed Jun. 23, 2000; Ser. No. 60/217,110, filed Jul. 10, 2000 and Ser. No. 60/223,212, filed Aug. 4, 2000.

FIELD OF THE INVENTION

The present invention relates to orally administered gastric retention systems and to pharmaceutical dosage forms that use them to release a drug in a patient's stomach.

BACKGROUND OF THE INVENTION

After the discovery of a new drug for treatment of a human disease, further investigation is undertaken to determine if the drug is most effectively administered to a patient intravenously, transdermally, subcutaneously or orally. Orally administered drugs are often favored whenever an oral route is feasible.

Pharmacokinetic studies can yield important information about how to get an optimum therapeutic response from a drug. For some drugs, maintaining a constant bloodstream and tissue concentration throughout the course of therapy is the most desirable mode of treatment. Immediate release of these drugs can cause blood levels to peak above the level required to elicit the desired response, which wastes the drug and may cause or exacerbate toxic side effects.

Many drugs provide better therapy when they are delivered in a controlled release manner. There are known dosage forms that are capable of sustaining or delaying release of a drug. In some sustained release dosage forms, the active ingredient is embedded in a matrix that slowly erodes to release the active ingredient. Other sustained and delayed release dosage forms have a coating. The coating on a sustained release dosage form may be semipermeable to the drug and thereby slow its release. The coating on some conventional delayed release dosage forms is impermeable to the drug and dissolves slowly in gastrointestinal fluid, thereby delaying release of the active ingredient until dissolution of the coating allows gastrointestinal fluid to contact the drug. However, semipermeable and impermeable coatings and conventional erodible matrices are often ineffective for sustained and delayed release of drugs with site specific absorption.

Many orally-administered drugs are most readily absorbed by the jejunum and duodenum. Other drugs are most readily absorbed through the stomach wall. Few drugs are efficiently absorbed by the colon. The residence time of a conventional dosage form in the stomach is 1 to 3 hours on average. After transiting the stomach, there is an approximately 3 to 5 hour window of bioavailability before the dosage form reaches the colon. Sustained or delayed release vehicles that are not retained in the stomach before and during release of the drug may release a significant portion of the drug after the window of bioavailability has passed. However, if the dosage form is retained in the stomach, the active ingredient will be released upstream of the small intestine and will enter the intestine in solution, a state in which it can be readily absorbed. Gastric retention dosage forms, i.e., dosage forms that are designed to be retained in the stomach for a prolonged period of time, can increase the bioavailability of drugs that are most readily absorbed by the upper gastrointestinal tract.

Another important application of gastric retention dosage forms is to improve the bioavailability of a drug that is unstable to the basic conditions of the intestine. A composition that is formulated to dissolve upon contact with any aqueous solution will at least partially dissolve in the stomach because it reaches the stomach before it reaches the intestine. However, unless the drug is very rapidly absorbed, or the residence time is increased, some of the drug will pass into the intestine. An unstable drug will at least partially decompose to a product compound that either is not absorbed or, if absorbed, may not exert the desired therapeutic effect. Accordingly, decomposition of a base sensitive drug that passes into the intestine reduces the effectiveness of the dosage and introduces an uncontrollable factor that is detrimental to accurate dosing.

Another important application of gastric retention is to deliver drugs to the active site for treatment of local disorders of the stomach, such as peptic ulcers.

For the foregoing reasons, pharmaceutical formulation specialists have developed strategies to increase the residence time of oral dosage forms in the stomach. One of the general strategies is intragastric expansion, wherein expansion of the dosage form prevents it from passing through the pylorus. The diameter of the pylorus varies between individuals from about 1 to about 4 cm, averaging about 2 cm. An expanding gastric retention dosage form must expand to at least 2 cm×2 cm in two dimensions to cause gastric retention, though a size of 2.5 cm×2 cm is more desirable.

One type of intragastric expanding dosage form uses hydrogels to expand the dosage form upon contact with gastric fluid to sufficient size to prevent its passage through the pylorus. An example of such a dosage form is described in U.S. Pat. No. 4,434,153. The '153 patent discloses a device for executing a therapeutic program after oral ingestion, the device having a matrix formed of a non-hydrated hydrogel and a plurality of tiny pills containing a drug dispersed throughout the matrix.

As noted in Hwang, S. et al. "Gastric Retentive Drug-Delivery Systems," *Critical Reviews in Therapeutic Drug Carrier Systems,* 1998, 15, 243-284, one of the major problems with intragastric expanding hydrogels is that it can take several hours for the hydrogel to become fully hydrated and to expand to sufficient size to cause it to be retained in the stomach. Since non-expanding dosage forms remain in the stomach on average for about 1 to 3 hours, there is a high probability that known expanding dosage forms like that of the '153 patent will pass through the pylorus before attaining a sufficient size to obstruct passage. The rate-limiting factor in the expansion of ordinary hydrogels is the rate of diffusion of water to non-surfacial hydrogel material in the dosage form. Conventional hydrogels are not very porous when they are dry, so transport of water into the hydrogel can be slow. In addition, a low permeability gelatinous layer forms on the surface of wetted hydrogel, which further slows transport of water into the hydrogel.

One approach to solving the problem of slow expansion has been the development of superporous hydrogels. Superporous hydrogels have networks of pores of 100μ diameter or more. At that diameter, the pores are able to rapidly transport water deep into the superporous hydrogel by capillary action. Water reaches the non-surfacial hydrogel material quickly resulting in a rapid expansion of the superporous hydrogel to its full extent. Superporous hydrogels are still under development and have not been approved for pharmaceutical use by the U.S. Food and Drug Administration. There are also shortcomings attendant to the use of superporous hydrogels. They tend to be structurally weak and some are unable to withstand the mechanical stresses of the natural contractions that propel food out of the stomach and into the intestine. The superporous hydrogels tend to break up quickly into particles too small to be retained.

Chen, J. and Park, K. *Journal of Controlled Release* 2000, 65, 73-82, describes a superporous hydrogel whose mechanical strength is improved by the polymerization of precursor hydrogel monomers in the presence of several superdisintegrants. The result of the polymerization described by Chen and Park is a new substance having interconnecting cross-linking networks of polyacrylate and, e.g., cross-linked carboxymethyl cellulose sodium. Such interconnecting networks are not expected to have the same physical properties as conventional hydrogels made from the same precursor hydrogel monomers.

Another general strategy for retaining dosage forms in the stomach is intragastric floatation, as exemplified in U.S. Pat. Nos. 4,140,755 and 4,167,558. Intragastric floatation systems are less dense than gastric fluid and avoid passage through the pylorus by floating on top of the gastric fluid. These systems generally take one of three forms. Hydrodynamically balanced floating systems comprise capsules of the active ingredient and a hydrogel that forms a gelatinous coating upon contact with water that slows further uptake of water. In one example of such a system, a capsule containing the non-hydrated hydrogel and an active ingredient dissolves upon contact with gastric fluid. The hydrogel then comes into contact with gastric fluid and forms a gelatinous coating on the surface. The gelatinous coating traps air inside the hydrogel thereby making the mass buoyant. Expansion of the hydrogel also makes it less dense and therefore more buoyant. Another form of intragastric floatation system is a gas generating system, which evolves gas upon contact with water. Gas bubbles trapped in the dosage form make it buoyant. Another variation on the intragastric floatation systems are low density core systems, wherein the active ingredient is coated over a low density material like puffed rice.

The floating dosage forms and expanding dosage forms previously described operate by different gastric retention mechanisms, each with its own requirements to be effective. A floatation system must remain buoyant even while absorbing gastric fluid. An expanding system must be capable of expansion to a size sufficient to obstruct transit into the intestine and yet be small enough in its non-hydrated state to be swallowed. The present invention includes embodiments that expand as well as embodiments that expand and generate gas.

There is a particular need for an effective gastric retention system for treatment of Parkinson's disease with levodopa. Parkinson's disease is a degenerative condition associated with reduced dopamine concentrations in the basal ganglia region of the brain. The deficiency is considered to be caused by oxidative degradation of dopaminergic neurons in the substantia nigra. The preferred course of therapy is to restore dopamine concentration in the brain by administration of levodopa, a metabolic precursor of dopamine that, unlike dopamine, is able to cross the blood-brain barrier. The metabolic transformation of levodopa to dopamine is catalyzed by the aromatic L-amino acid decarboxylase enzyme. This enzyme is found throughout the body including gastric juices and the mucosa of the intestine. Treatment with levodopa alone requires administration of large doses of the drug due to extracerebrial metabolism by this enzyme. The resulting high concentration of extracerebrial dopamine causes nausea in some patients. To overcome this problem, levodopa is usually administered with an inhibitor of the aromatic L-amino decarboxylase enzyme such as carbidopa.

Levodopa eases the symptoms of Parkinsonism by temporarily boosting dopamine concentration in the central nervous system, but it is not a cure. During prolonged treatment of the disease with levodopa, the body typically becomes less sensitive to levodopa concentration in the brain. The body requires more frequent dosing to suppress the manifestations of the disease: tremor, muscular rigidity, lack of facial expression, and altered gait. As the blood plasma concentration drops, the return of disease manifestations in the so-called "off state," signals the need for immediate administration of another dose. There is, unfortunately, a delay between ingestion of levodopa and a return to the "on state" suppression of the disease symptoms. Aggressive administration of levodopa to circumvent off state symptoms of rigidity and akinesia, can lead to equally disabling involuntary motions called dyskinesias.

From the foregoing, it will be appreciated that it is highly desirable to be able to administer levodopa as a sustained release oral dosage form capable of stabilizing the serum level of levodopa in a patient. Levodopa/carbidopa is currently available in Sinamet® CR controlled release tablets (DuPont Pharma) that slowly erode to release the actives. According to the *Physician's Desk Reference*, 54th ed., the tablets use a polymeric based drug delivery system. Prolonged suppression of disease manifestations with these tablets is limited by the mechanism of absorption of levodopa from the gastrointestinal tract. Levodopa is absorbed by the active transport mechanism for amino acids, which is most active in the duodenum region of the small intestine. Sustained release is therefore limited by the transit time of the dosage form through the stomach and duodenum which, though highly variable from individual-to-individual and dependent upon nutritional state, typically takes only about 3 to 4 hours. Levodopa released after the 3-4 hour therapeutic window has passed is not bioavailable. Sinemet® CR controlled release tablets have about 75% of the bioavailability of Sinemet® conventional release tablets. *Physicians Desk Reference,* 54th edition (Medical Economics Co., publisher, 2000) at p. 979.

Another problem in Parkinson's disease therapy that could be addressed with an improved controlled release levodopa delivery vehicle is the reduction in plasma levodopa concentration that occurs while a patient is sleeping. Parkinson's patients usually awaken in the morning in the off state and must wait for a morning dose of levodopa to take effect before they can function comfortably. It would be highly desirable if a Parkinson's disease patient could take levodopa in the evening, while under the therapeutic effect of a previous dose, and wake up in the morning without the manifestations of the disease. For such purpose, the drug delivery vehicle ideally would not only extend the release of levodopa over time, but would also delay release of levodopa until the early morning hours before the patient awakens so that the patient would awaken when the therapeutic effect of the dose is near its maximum.

Therefore, there is a need for a controlled release levodopa oral dosage form that is able to deliver levodopa to a patient's bloodstream over a longer time period than is currently possible without resort to a regimen of frequent dosing, and the fluctuations in plasma levodopa levels that occur with frequent dosing. Further, there is a need for improvement in controlled-release forms that improves the bioavailability of levodopa as well as lowers the dosage frequency.

There is also a particular need for an effective gastric retention system for use in treatment of children with hyperactivity and attention deficit disorder. Methylphenidate, the mainstay in treatment of hyperactivity, has a short half-life in the human body and, so, frequent dosing (about every four hours) is required. Children therefore need to take the drug when they are in school. This poses administrative problems for schools that are asked to see that a child takes his medication. Sustained release formulations of methylphenidate have been developed. Methylphenidate is currently available in Ritalin®-SR sustained-release tablets (Novartis). According the *Physician's Desk Reference*, 54th ed., Ritalin®-SR tablets contain cellulose compounds and povidone. Another sustained release formulation of methylphenidate is proposed in U.S. Pat. No. 5,874,090. Unfortunately, patients become tolerant to a sustained high blood level of methylphenidate and require more medication to suppress their hyperactivity or distractibility.

U.S. Pat. No. 6,034,101 (and WO 98/14168) discloses a methylphenidate dosage form that is designed to overcome the development of tolerance within a single dosage interval. This dosage form delivers methylphenidate in pulses of ascending intensity. However, the dosage form is not a gastric retention form. Therefore, while the first pulse of drug is released in the stomach, subsequent pulses are delivered in the jejunum, ileum, and/or colon. Methylphenidate is more readily absorbed by the stomach than by the intestine. Consequently, the pulses that are designed to be the most intense are the least bioavailable because they are released downstream of the stomach. Another dosage form for delivering methylphenidate in pulses is described in U.S. Pat. No. 5,837,284. In addition to the mismatch between the ascending dose profile and the descending bioavailability as the dosage form passes through the GI tract, these pulsed methods have the drawback that the higher dosages can increase the severity and occurrence of the side effects experienced with the drug, especially sleep disturbance.

Allowing a sufficiently long drug-free interval between doses of methylphenidate is a more preferred approach to avoid acute tolerance than using an ascending drug profile. However, the pulse delivery systems used to deliver methylphenidate over greater periods of time suffer the same bioavailability problems as the pulsed dosage forms with ascending profiles. Thus, there is a need for a gastric retention pulsed delivery system that can deliver methylphenidate in pulses with consistent bioavailability.

There is clearly a need for improvement in gastric retention-controlled release technology and a particular need for improved gastric retention dosage forms of levodopa and methylphenidate.

OBJECTS AND SUMMARY OF THE INVENTION

Figure 1:
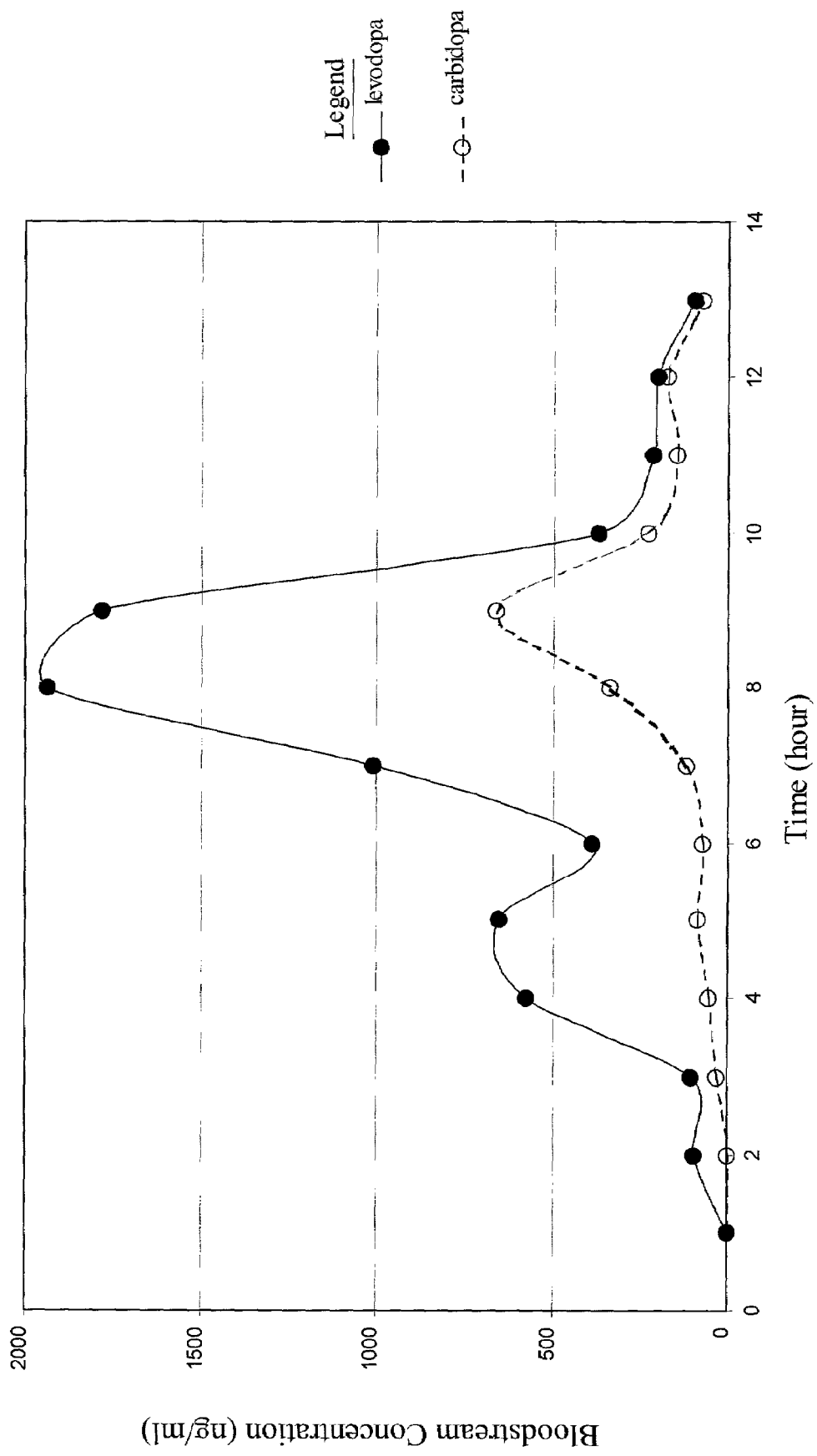
FIG. 1 is a plot showing the blood level concentration of levodopa and carbidopa in a beagle dog over time after administration of a delayed release levodopa and carbidopa dosage form of this invention.

We have now discovered a composition that expands rapidly in the gastric juices of a patient, thereby increasing the likelihood that the composition will be retained in the stomach for a prolonged period of time. This composition is a blend of a superdisintegrant, tannic acid and one or more hydrogels. The composition is useful in gastric retention dosage forms because it increases the likelihood that an active ingredient carried by the form will be released in the stomach.

A dosage form of the present invention expands rapidly, at a rate not previously attainable with known expanding hydrogel formulations, yet because it does not contain a superporous hydrogel, it avoids the mechanical strength problems associated with superporous hydrogels. An additional advantage of using conventional hydrogels in the inventive composition and dosage forms is that the degradation/erosion rates of these hydrogels are well studied.

The present invention provides a pharmaceutical composition for use in an orally administered pharmaceutical product that expands upon contact with gastric fluid to promote retention of a dosage form in the patient's stomach for a prolonged period of time. The composition comprises a nonhydrated hydrogel, a superdisintegrant and tannic acid, preferably in amounts, exclusive of any other excipients that may be present, of from about 20 wt. % to about 70 wt. % hydrogel, from about 10 wt. % to about 75 wt. % superdisintegrant and from about 2 wt. % to about 12 wt. % tannic acid.

In one embodiment, the pharmaceutical composition comprises from about 10 wt. % to about 20 wt. % hydroxypropyl methylcellulose ("HPMC"), from about 45 wt. % to about 50 wt. % hydroxypropyl cellulose ("HPC"), about 25 wt. % to about 35 wt. % sodium starch glycolate and about 4 wt. % to about 6 wt. % tannic acid. A second embodiment of the pharmaceutical composition comprises from about 10 wt. % to about 30 wt. % hydroxypropyl methylcellulose, from about 40 wt. % to about 60 wt. % hydroxypropyl cellulose, about 7 wt. % to about 35 wt. % sodium crosscarmelose and about 4 wt. % to about 12 wt. % tannic acid. These compositions can expand in volume five fold or more within about fifteen minutes by imbibing water from gastric fluid.

The present invention further provides orally administered pharmaceutical dosage forms containing a therapeutic agent and the pharmaceutical composition. The forms can be used to deliver the therapeutic agent to the stomach of the patient in an immediate or controlled release manner. For instance, in one of the dosage forms, the therapeutic agent is provided as coated particles which are dispersed throughout a matrix comprising the pharmaceutical composition of the present invention. This form is well suited for delayed and pulsed delivery of the therapeutic agent. In another dosage form embodiment, the therapeutic agent is contained in a sustained release reservoir embedded in a shell comprising the composition of the present invention. The shell promotes retention of the dosage form in the patient's stomach while the therapeutic agent is released in a sustained manner from the reservoir.

The present invention further provides dosage forms for controlled gastric release of levadopa and controlled gastric release of methylphenidate. These dosage forms are adapted to address problems with current therapies that use these drugs. The present invention therefore further provides methods of treating diseases with these drugs, and other drugs, by administering the dosage forms and compositions of this invention.

DETAILED DESCRIPTION OF THE INVENTION

The terms "drug," "actives," "active ingredient," "therapeutically beneficial agent" and "therapeutic agent" are all used interchangeably in this disclosure and mean a compound that exerts a therapeutically beneficial effect on a patient and prodrugs, solvates, molecular complexes and pharmaceutically acceptable salts and derivatives of the compound.

The term "gastric fluid" means the endogenous fluid medium of the stomach, including water and secretions, or simulated gastric fluid. "Simulated gastric fluid" means any fluid that is generally recognized as providing a useful substitute for authentic gastric fluid in experiments designed to assess the chemical or biochemical behavior of substances in the stomach. One such simulated gastric fluid is USP Gastric Fluid TS, without enzymes. *United States Pharmacopeia and National Formulary* 24/19 p. 2235 (1999). Thus, it will be understood that throughout this disclosure and in the claims "gastric fluid" means authentic gastric fluid or simulated gastric fluid.

"Immediate release" means that release of the active ingredient is not significantly delayed by means of a protective coating or embedding in a matrix. The excipients used to achieve immediate release typically dissolve or disperse rapidly in gastric fluid. "Sustained release" means release of the active ingredient from the dosage form over a longer period of time than the immediate release time for the same quantity of the same active ingredient from an equivalent dosage in an immediate release formulation. "Delayed release" means that there is a period of time after the dosage form contacts gastric fluid during which the active ingredient either is not released or is released at a rate that is not therapeutically effective for the purpose that the drug has been administered to the patient. "Burst release" means release of most of the active ingredient over a short period of time, typically less than 30 minutes. "Pulsed release" means release of the active ingredient over two or more time periods separated by a period of time in which either the active ingredient is not release or is released at a rate that is not therapeutically effective for the purpose that the drug has been administered to the patient. Burst release, pulsed release and sustained release may be coupled with delayed release so that release of the active ingredient according to that profile begins after a delay period in which the active ingredient either is not released or is released at a rate that is not therapeutically effective for the purpose that the drug has been administered to the patient. The term "controlled release" is used inclusively to mean delayed release; sustained release, including delayed sustained release; burst release, including delayed burst release; pulsed release, including delayed pulsed release; and any release other than immediate release.

The present invention provides a gastric retention composition that expands rapidly upon contact with the gastric juices of a patient. The expanding composition is advantageously used as a gastric retention delivery system ("GRDS") in an orally administered pharmaceutical dosage form to increase the likelihood that the dosage form will be retained in a patient's stomach for a prolonged period of time.

After the expanding composition is hydrated and expanded, it allows solubilized substances inside the expanded composition to diffuse into the surrounding fluid environment. Thus, the expanding composition is well suited for use in a delayed, burst and/or pulsed release dosage form. The expanding composition is also well suited for use with a reservoir designed to deliver a drug in a sustained release manner. The reservoir may be a sustained release core embedded in the expanding composition; it may be a tablet enclosed within a capsule along with the expanding composition or it may be a layer of a multi-layer construction in which the reservoir layer contains the active ingredient and is provided with means for releasing the active ingredient in a sustained manner and the other layer contains the expanding composition. The expanding composition is also well adapted for use with sustained release particles in which a coating is applied to the particle which slows the release of the active ingredient or with sustained release particles in which the active ingredient is dispersed in a particle matrix that slows release of the active ingredient. The expanding composition also may be used to slow the release of the active ingredient.

The composition's rapid rate of expansion has clinical implications. There is a chance that any expanding gastric retention dosage form will pass through the stomach before it has expanded sufficiently to be retained. If the drug happens to be administered to a patient shortly before peristalsis, the dosage form may pass out of the stomach in much less time than the average residence time. After an incompletely expanded dosage form is passed into the intestine, further expansion may cause blockage of the patient's intestine for a period of time. The window of bioavailability also may be missed, especially if the active ingredient is most readily absorbed in the stomach or is unstable to basic conditions. The likelihood that an expanding dosage form will pass through the stomach before it attains a size sufficient to block passage through the pylorus depends upon many factors such as the fasting or fed state of the patient and the gastric motility of the patient. In a fasting state, conventional oral dosage forms are emptied from the stomach about every one hundred minutes by gastric peristalsis. Another factor over which the present invention gives the clinician control is the relationship between amount of time required for the dosage form to expand and the time it takes for gastric emptying. Thus, it will be appreciated that a rapid rate of expansion is a significant advantage of the present invention.

Another aspect of the invention provides dosage forms containing the expanding composition of the present invention. Dosage forms according to this invention are retained in the stomach for an extended period of time by expansion of the composition and, optionally, by floatation. In an embodiment that uses floatation for improved gastric retention, the dosage form contains a substance that effervesces on contact with aqueous or aqueous acidic solution. The expanded composition traps some of the bubbles given off by the effervescent substance thereby making the dosage form buoyant. Gastric retention causes the active ingredient to be released upstream of the jejunum and duodenum, which are the two segments of the GI tract which most actively absorb many drugs. Over time the expanded dosage form degrades or erodes into particles that are sufficiently small to pass through the pylorus.

Rapid expansion of the composition and dosage forms containing it is achieved with a novel combination of hydrogel, superdisintegrant and tannic acid.

Hydrogels are polymers that are hydrophilic but insoluble in water. In their hydrated condition they swell to an equilibrium volume, are elastically deformable but virtually immune to plastic deformation. In their dry state, hydrogels may be structurally rigid. The preferred hydrogel of the expanding composition is hydroxypropyl methylcellulose, either alone or in combination with hydroxypropyl cellulose and/or a cross-linked acrylate polymer. Preferably, the HPMC has a molecular weight of from about 4000 to about 100,000 a.u. and a viscosity grade of about 8000 mPa·s or less. HPMC is commercially available under the trade name Methocel® from Dow Chemical Co.

Hydroxypropyl cellulose used in the expanding composition preferably has a molecular weight in the range of from about 80,000 to about 1.2 million, more preferably from about 1.0 million to about 1.2 million. HPC is commercially available under the trade name Klucel® from Hercules Inc.

Suitable cross-linked acrylate polymers include polyacrylic acid crosslinked with allyl sucrose commercially available under the trade name Carbopol® (BF Goodrich Chemical Ltd.) and polyacrylic acid cross linked with divinyl glycol.

The most preferred hydrogel of the present invention is a combination of hydroxypropyl methylcellulose and hydroxypropyl cellulose in a weight ratio of from about 1:3 to about 5:3.

The expanding composition also includes a superdistintegrant. Superdisintegrants are disintegrants that expand upon contact with water. Preferred superdisintegrants of the present invention expand to at least double their non-hydrated volume on contact with water. Exemplary of these superdisintegrants are cross-linked carboxymethyl cellulose sodium (a.k.a. croscarmellose sodium), sodium starch glycolate and cross-linked polyvinyl pyrollidone (a.k.a. crospovidone). Croscarmellose sodium is commercially available from FMC Corp. under the tradename Ac-Di-Sol® and from Avebe Corp. under the tradename Primellose®. Sodium starch glycolate is commercially available from Penwest Pharmaceuticals Co. under the tradename Explotab® and from Avebe Corp. under the tradename Primojel®. Crospovidone is commercially available from BASF Corp. under the tradename Kollidon® CL and from International Specialty Chemicals Corp. under the tradename Polyplasdone®. The most preferred superdisintegrant is croscarmellose sodium.

The expanding composition further includes tannic acid. Tannic acid, also called tannin, gallotannin and gallotannic acid, is a naturally occurring constituent of the bark and fruit of many trees. The term "tannins" conventionally refers to two groups of compounds, "condensed tannins" and "hydrolyzable tannins." *Merck Index* monograph No. 8828 (9th ed. 1976). The hydrolyzable tannins are sugars that are esterified with one or more (polyhydroxylarene) formic acids. One common polyhydroxylarene formic acid substituent of tannic acid is galloyl (i.e. 3,4,5-trihydroxybenzoyl). Another common polyhydroxylarene formic acid substituent of tannic acid is meta-digallic acid. A common sugar moiety of tannic acid is glucose. Preferably, USP grade tannic acid is used.

The expanding composition comprises a hydrogel, preferably hydroxypropyl methylcellulose optionally in combination with other hydrogel polymers, a superdisintegrant and tannic acid, preferably in an amount, exclusive of any other excipients that may be present, of from about 20 wt. % to about 70 wt. % hydrogel, from about 10 wt. % to about 75 wt. % superdisintegrant and from about 2 wt. % to about 12 wt. % tannic acid. An especially preferred expanding composition comprises from about 30 wt. % to about 55 wt. % superdisintegrant, about 5 wt. % (±2 wt. %) tannic acid, plus an amount of hydrogel sufficient to bring the total to 100 wt. %.

As previously mentioned, a preferred hydrogel for the expanding composition is hydroxypropyl methylcellulose, optionally in combination with hydroxypropyl cellulose or a cross-linked acrylate polymer. An expanding composition in which a preferred hydrogel is used preferably comprises from about 10 wt. % to about 30 wt. % hydroxypropyl methylcellulose, from about 40 wt. % to about 60 wt. % hydroxypropyl cellulose, from about 7 wt. % to about 35 wt. % croscarmellose sodium and from about 4 wt. % to about 12 wt. % tannic acid.

A second preferred embodiment of the expanding composition in which the preferred hydrogel is used comprises from about 10 wt. % to about 20 wt. % hydroxypropyl methylcellulose, from about 45 wt. % to about 50 wt. % hydroxypropyl cellulose, about 25 wt. % to about 35 wt. % sodium starch glycolate and about 4 wt. % to about 6 wt. % tannic acid.

Within these ranges, there are preferred formulations in dosage forms designed for particular applications, as described in detail below. In particular, a matrix type dosage form for delayed release of levodopa or a mixture of levodopa and carbidopa is provided. An especially preferred expanding composition for the matrix of a delayed release levodopa/carbidopa dosage form contains from about 10 wt. % to about 14 wt. % HPMC, from about 42 wt. % to about 47 wt. % HPC, from about 7 wt. % to about 12 wt. % croscarmellose sodium, from about 6 to about 9 wt. % tannic acid, from about 18 wt. % to about 22 wt. % levodopa from about 3 wt. % to about 6 wt. % carbidopa and from about 0.3 wt. % to about 1 wt. % tablet lubricant such as magnesium stearate.

An especially preferred formulation of the expanding composition for use as a shell in a reservoir dosage form of levodopa, levidopa/carbidopa, methylphenidate or alendronate comprises from about 10 wt. % to about 20 wt. % HPMC, from about 50 wt. % to about 60 wt. % HPC, from about 12 wt. % to about 25 wt. % croscarmellose sodium, from about 8 wt. % to about 12 wt. % tannic acid and from about 0.5 wt. % to about 1 wt. % of a tablet lubricant such as magnesium stearate.

The novel expanding composition of the invention can be prepared conventionally by dry blending, dry granulation or wet granulation.

In dry granulation, the composition is blended dry and then compacted into a slug or a sheet and then comminuted into compacted granules. It will be appreciated that the processes of slugging or roller compaction, followed by comminution and recompression render the hydrogel, superdisintegrant and tannic acid intragranular in the final dosage form. The active ingredient of the pharmaceutical may also be provided intragranularly by blending it with the expanding composition prior to compaction. Alternatively, the active ingredient, hydrogel, superdisintegrant or tannic acid may be added after comminution, which results in that (or those) ingredient(s) being extragranular. The granulate may be used to prepare a dosage form by any of the methods described below or any other means.

In wet granulation, the excipients may be granulated using a water:alcohol mixture or an alcohol as a granulation solvent by standard granulation techniques known in the art. The granulate may then be dried and optionally milled and sieved. The hydrogel, superdisintegrant, tannic acid or active ingredient may be added to one or more of the wet granulated ingredients either before or after compaction, in which case an ingredient added after granulation would be extragranular in the final dosage form. After drying, the granulate prepared by wet granulation may be used to prepare a dosage form by any of the methods described below or any other means.

The composition may be compacted following conventional compression and direct compression techniques. Direct compression produces a more uniform tablet without granules. Thus the hydrogel, superdisintegrant, tannic acid, the active ingredient(s) and any other desired excipients are blended with the composition prior to direct compression tableting. Such additional excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in the particular formulation challenges of direct compression tableting.

In some dosage forms, controlled release of the active ingredient may be provided by applying a coating to the active ingredient. Thus, where the foregoing description of the present invention has described mixing, blending, granulating, compressing, etc. of the active ingredient, it will be appreciated by those skilled in the art that the active ingredient may previously be coated with a coating.

The preceding description is intended to highlight variations of compounding techniques already well known in the art. However, the composition can be used with any chemically compatible drug in any manufacturing process. Specific novel and therapeutically useful gastric retention dosage forms are disclosed below.

The pharmaceutical dosage forms of the present invention comprise an active ingredient and a drug delivery vehicle comprising the expanding composition of the invention and any other desired pharmaceutical excipients. Pharmaceutical dosage forms of this invention can be retained in the stomach for three hours or more, more preferably about five hours or more. The dosage forms of the present invention are capable of expanding in volume by a factor of about three or more, about five or more if an expanding composition according to the preferred embodiments is used and, about eight or more if an expanding composition according to the most preferred embodiments is used. Expansion occurs within about fifteen minutes of contacting gastric fluid, within about five minutes when formulated according to the preferred embodiments.

Further improvement in gastric residence time may be realized by adding an effervescent compound that produces gas when contacted with gastric fluid, such as sodium bicarbonate. In a dry granulation process, the effervescent compound may be introduced into the dosage form by blending it into the expanding composition before or after first compaction. In a wet granulation process, it may be provided as an extragranular constituent after wet granulation. Further the effervescent compound may be a constituent of a reservoir in reservoir-type dosage form. The effervescent compound is preferably used at low concentration, i.e. from about 0.5 wt % to about 5 wt. % of the dosage form. In addition to sodium bicarbonate, effervescent compounds include, for example, other alkali and alkaline-earth metal carbonates and bicarbonates.

Mucoadhesive substances also may be added to enhance gastric retention of dosage forms prepared according to the present invention.

One gastric retention dosage form embodiment is a tablet which may be prepared by compacting the expanding composition, active ingredient(s) and, optionally, other excipients, as a powder blend or granulate in any type of tableting equipment known to the pharmaceutical arts. Another dosage form is a capsule, which may be prepared by filling a conventional capsule shell (e.g., gelatin) with a powder blend, granulate or tablet containing the expanding composition, active ingredient(s) and, optionally, other excipients.

Dosage forms of the present invention may be made in any shape desired. Ovoid or elliptical shaped dosage forms are well retained after expanding to their full extent. An ovoid or elliptical dosage form preferably is sized at between about 4 mm and 10 mm in two dimensions and between about 10 mm and 20 mm in the third dimension, more preferably 6×6×16 mm±2 mm.

There is a wide variety of dosage forms and ways to use the expanding composition in the dosage forms of the present invention.

Dosage forms may be a matrix type in which the active ingredients(s) are particles uniformly dispersed throughout the expanding composition. In a matrix construction, the particles of active ingredient(s) may be a milled powder or granulate. The particles also may be pre-formulated beads, pills, pellets, microcapsules, microspheres, microgranules, nanocapsules or nanospheres and the like containing or having on their surface the active ingredient. These preformulated particles are dispersed in the matrix.

A pre-formulated particle may contain the powdered active ingredient in a natural, semi-synthetic or synthetic polymer matrix. Representative matrices for dispersed particles are polysaccharides, agar, agarose, sodium alginate, carrageenan, gum arabic, tragacanth gum, locust bean gum, pectin, amylopectin, gelatin, starch, microcrystalline cellulose and hydrogels. Further particle matrices can include crosslinked gelatin, crosslinked albumin, crosslinked sodium alginate, crosslinked carboxymethylcellulose, crosslinked polyvinyl alcohol and crosslinked chitin as described in U.S. Pat. No. 5,007,790.

The active ingredient(s) may be contained in coated particles, e.g., beads, tiny pills, microspheres, nanospheres and microgranules that have been coated with a substance or substances that are impermeable or semipermeable to the active ingredient and/or slowly dissolve in gastric fluid. A coating may be used to slow the release of the active ingredient or to delay the release of the active ingredient. A delay release coating is impermeable to the active ingredient until the coating is breached by the gastric fluid. Dosage forms of the matrix type may be formulated for delayed release using coated particles. The expanding composition will retain the dosage forms in the stomach until the delay time has passed, whereupon the drug is released.

Particles may be coated with known film coating agents such as water soluble resins, such as arabinogalactan, carboxymethylcellulose, gelatin, gum arabic, hydroxyethylcellulose, methylcellulose, polyvinyl alcohol, polyacrylic acid, and starch; water insoluble resins, such as cellulose nitrate, ethyl cellulose, e.g., Ethocel™; cellulose nitrate, polyamide, polyethylene, poly(ethylene-vinyl acetate), poly(lactide-co-glycolide), polymethacrylate, e.g., Eudragit™ NE, Eudragit™ RS, Eudragit™ RL, Eudragit™ L and Eudragit™ S and silicones; waxes and lipids such as paraffin, carnauba wax, spermaceti, beeswax, stearic acid stearyl alcohol and glyceryl stearates; and enteric resins such as cellulose acetate phthalate, polyvinyl acetate and hydroxypropyl methylcellulose acetate. The glyceryl esters may be mixed with a wax as previously described in U.S. Pat. No. 4,764,380, which is incorporated by reference in its entirety. Such a coating may be made from triglyceryl esters like glyceryl distearate, glyceryl tristearate, glyceryl monostearate, glyceryl dipalmitate, glyceryl tripalmitate, glyceryl monolaurate, glyceryl didocosanoate, glyceryl tridocosanoate, glyceryl monodocosanoate, glyceryl monocaprate, glyceryl dicaprate, glyceryl tricaprate, glyceryl monomyristate, glyceryl dimyristate, glyceryl trimyristate, glyceryl monodecenoate, glyceryl didecenoate and glyceryl tridecenoate. Waxes that may be used include beeswax, cetyl palmitate, spermacetic wax, carnauba wax, cetyl myristate, cetyl palmitate, ceryl cerotate, stearyl palmitate, stearyl myristate and lauryl laurate. Particles coatings may also be from other polymeric coating substances which include methylcellulose phthalate, poly(alkyl methacrylates), poly(alkyl cyanoacrylates), polyglutaraldehyde, poly(lactide-glycolide) and albumin. Additional coating materials that may be used are disclosed in U.S. Pat. Nos. 4,434,153; 4,721,613; 4,853,229; 2,996,431; 3,139,383 and 4,752,470, which are hereby incorporated by reference in their entirety.

Particles coated with delayed release coatings may be advantageously used to produce a dosage form for pulsed release of the active ingredient(s). For example, one could deliver two, three (or more) timed doses in a pulse fashion while the patient needs to take the dose only once. The three doses would mimic taking multiple doses of the drug at the prescribed times, with the drug being absorbed from the stomach or upper intestine with each dose. Such dosing allows for improved compliance to dosage schedules and in many cases will lead to improved therapy. Delayed dosage forms that do not include gastric retention will deliver each such dose in a different part of the GI tract with different absorption profiles for each of the doses. Such therapy would not be equivalent to taking three doses of the drug at the prescribed times, wherein the drug would have been absorbed from the stomach or upper intestine in each case. For this purpose, particles may be provided with coatings of different thicknesses. Alternatively, the particles may be coated with different substances having different dissolution rates in gastric fluid.

Gastric fluid rapidly penetrates the expanding dosage form because of the hydrophilicity and porosity of the expanding composition. Consequently, the coated particles contact gastric fluid approximately simultaneously regardless of their proximity to the outer surface of the dosage form. The coatings of a certain proportion of particles, either those with a thin coating or a relatively soluble coating, are breached nearly simultaneously. This causes release of the active ingredients(s) from those particles over a short time period, i.e., in a pulse. A second pulse occurs when the coating of particles having either a thicker coating or a coating of a slower dissolving substance is breached. The timing and intensity of the pulses can be determined by the formulator using knowledge available about the dissolution rates of coating substances and by routinely selecting the proportion of each type of coated particle to match the intensity of the pulse desired.

A pulsed release may be used to deliver one, two or more active ingredients at different times after the patient has swallowed the dosage form.

In a coated pulsed release dosage form, the core of the particle preferably can be either one or more active ingredients or a mixture of the active ingredient(s) with excipients that do not retard release of the active ingredient(s). Even if the particle core contains excipients that in certain applications retard release of actives, such as high molecular weight polyvinyl pyrollidone, rapid release may occur nevertheless due to the small volume and relatively large surface area of the particles.

In a hydrated state, the expanding compositions of this invention do not necessarily limit diffusion of a solubilized active ingredient into the gastric environment. Therefore, the pulsed release of active ingredient inside of the expanded dosage form may translate into pulsed release into the gastric fluid.

The composition is also suited for the retention of drugs in the stomach when such drugs are contained in tablets that are either partially embedded in the expanding composition or attached thereto by an adhesive. These tablets can be of a slow release nature giving slow or controlled release for an extended period of time in the stomach. These tablets can further be of a delayed pulse release nature. The expanding composition of this invention will retain these forms in the stomach until the delay time has passed whereupon the drug will be released in a burst or pulse fashion. Attaching, or partially embedding, several such tablets, each timed with a different delay to release, to the composition of this invention, allows versatile dosing schemes from one taken dose. For example one could deliver three (or more) timed doses in a pulse fashion while the patient needs to take the dose only once. The three doses would mimic taking three doses of the drug at the prescribed times, with the drug being absorbed from the stomach with each dose. Such dosing allows for improved compliance to dosage schedules and in many cases will lead thereby to improved therapy. Delayed dosage forms that are not coupled to gastric retention will deliver each such dose in a different part of the GI tract with different absorption profiles for each of the doses. Such therapy would not be equivalent to taking three doses of the drug at the prescribed times, wherein the drug would have been absorbed from the stomach in each case.

Dosage forms may be a reservoir (depot) type. Reservoir forms contain the active ingredient in a reservoir that is embedded in a shell of any desired thickness that does not cause the dosage form to be too large to be swallowed by the patient. Embedded tablets and tablets with cores are examples of reservoir type of dosage forms. A reservoir type further includes capsule forms, multilayer forms and other forms wherein the active ingredient is separated from the expanding composition. The reservoir may be fully embedded in a shell of the expanding composition or it may be partially embedded so that a portion of the surface of the reservoir is exposed. A reservoir may be a tablet enclosed within a capsule along with a tablet containing the expanding composition. These types of products may be manufactured using methods known in the art.

The reservoir may be formulated to be either immediate release or controlled release. The release profile of the dosage form may be made to approximate the release profile of the reservoir (even when the reservoir is completely embedded in the expanding composition) because the hydrated and expanded composition does not necessarily inhibit diffusion of solubilized substances into the gastric environment. For example, an immediate release reservoir may be prepared by blending an active ingredient(s) with microcrystalline cellulose, lactose and magnesium stearate and compressing the blend into a compacted reservoir. For another example, a sustained release reservoir may be prepared by direct compression of the active with about 5-75% hydroxypropyl methylcellulose, such as Methocel® K15M, K100LV, K4M, K100M, E4M and E10M, lactose and magnesium stearate.

The reservoir may also be attached to the expanding composition with an adhesive. The expanding composition is compacted into a tablet ("GRDS tablet"). The reservoir can be attached by adhesive during manufacture by depositing a drop of adhesive on a GRDS tablet as it leaves the punch station in the tableting machine and having a device push the reservoir, e.g., another tablet, containing the drug against the deposited adhesive.

More preferably, the drug containing reservoir can be adhered to the GRDS tablet in situ the stomach by coating the GRDS tablet with an aqueous based adhesive that does not interfere with its swelling properties and loading the GRDS tablet and one or more drug reservoirs(s) into an appropriately sized gelatin capsule where the GRDS tablet is physically in contact with the drug reservoir(s) to be adhered to it. When water enters the capsule, the adhesive is wetted and adheres the drug reservoir(s) due to their proximity in the capsule prior to the GRDS system's rapid swelling. The tablets remain adhered to each other after the swelling. Preferred water based adhesives for this use are protein adhesives such as gelatin, egg albumin, and casein their salts and derivatives and polysaccharide adhesives such as starch, modified starches, and other polysaccharide derivatives known in the art as glues. The most preferred adhesive for in situ adhesion of the drug reservoir to the GRDS unit is sodium caseinate available commercially as Emulac™ 50.

A reservoir may be coated with a conventional sustained release coating. Such coating materials include polymethacrylate, e.g., Eudragit™ NE, Eudragit™ RS, Eudragit™ RL, Eudragit™ L, Eudragit™ S, and mixtures of hydrophilic and hydrophobic film forming agents. Hydrophilic film forms include methyl cellulose, hydroxypropyl methylcellulose, cellulose phthalate, cellulose acetate phthalate and polyvinyl alcohol. Hydrophobic film forming agents include ethyl cellulose, cellulose acetate, hydroxypropyl methylcellulose phthalate, polyvinyl alcohol maleic anhydride copolymers, β-pinene polymers rosin, partially hydrogenated rosin and glycerol esters of rosin. A sustained release coating may be applied by methods known in the art such as by fluid bed or pan coating techniques.

In addition to being of an immediate release or sustained release nature, the reservoir can further be of a delayed pulse release nature or a delayed sustained release nature.

Dosage forms of the present invention may also have a layered construction wherein the actives, alone or in mixture with any other excipients, form a layer that is bonded, e.g., by compression, to another layer containing the expanding composition. Preferred dimensions for a layered dosage form are about 14×8 mm±2 mm. A layered construction may be prepared by conventional multilayer compression techniques. A layered dosage form comprising two or more layers, one comprising the expanding composition and another comprising the actives and any other desired excipients, may be made to delay release of the actives by coating only the actives-containing layer with a conventional coating resistant to gastric fluids. A further method of achieving a delay in the release is to formulate the drug-containing layer as a matrix that delays diffusion and erosion or by incorporating the active substances in microcapsules or coated beads within the drug-containing layer.

One preferred active ingredient for use in the dosage forms of the present invention is methylphenidate. Especially preferred dosage forms for pulsed delivery of methylphenidate are the following tablet and capsule forms.

One preferred pulsed release methylphenidate tablet contains coated particles or multiple coated reservoirs dispersed in a matrix or shell comprising the expanding composition. In each case, the particle or reservoir is coated with a suitable coating as previously described. In such methylphenidate tablets containing particles, a portion of the plurality of particles may be uncoated for immediate release. A second proportion of the particles is coated to release a second pulse (after the immediate pulse) of methylphenidate preferably from about 3 to about 5 h after the tablet is administered to the patient. There may also be a third proportion of particles that is coated to release about 4 h after the second pulse. Timing the pulses about 4 h apart provides an interval of low methylphenidate concentration in the bloodstream that resists development of acute tolerance. In reservoir-containing tablets, the number of reservoirs corresponds to the number of pulses desired, typically two or three. One of the reservoirs may be uncoated for immediate release while the others are coated so as to release the methylphenidate within the same time ranges specified above as preferred release times from particles.

An especially preferred capsule dosage form for pulsed delivery of methylphenidate contains two tablets (reservoirs) containing the drug and coated for timed delay of release. These two tablets are placed in contact with a coated GRDS tablet that has an adhesive such as sodium caseinate and an immediate release dose of methylphenidate as its coating. When the capsule enters the stomach, the gelatin capsule dissolves, the adhesive coating on the GRDS is wetted and causes adhesion of the drug containing tablets to the GRDS tablet, the immediate dose of methylphenidate is released and the GRDS tablet swells for gastric retention. The three tablet ensemble is retained in the stomach for an extended period. At the predetermined time, e.g. 4 hours, the second dose is released. The third dose is released at the second predetermined time e.g. 8 hours.

In a methylphenidate pulsed release capsule, one tablet may be an immediate release formulation and the second tablet may be a delayed release formulation, though both may be delayed release. There will be some delay in release from an immediate release tablet due to the time required to dissolve the capsule. An immediate release formulation may be a tablet prepared as described by any of the methods above, or other method, in which the methylphenidate is dispersed as a powder, or as an ingredient of a particle, throughout the tablet matrix. A delayed release tablet is preferably a matrix type with a delayed release coating around the tablet. Such a tablet, therefore, may contain methylphenidate dispersed as a powder or as an ingredient of an immediate release particle. Two or more delayed release tablets may be provided in the capsule, which have coatings of different substances, or of different thicknesses so as to release the methylphenidate at different times. The preferred release time for a first delayed release tablet is from about 4 h to about 5 h after the drug is administered to a patient. Successive delayed-release pulses from additional delayed release tablets that may be provided in the capsule preferably occur in intervals of about 4 to about 5 h.

Whether a pulsed release methylphenidate dosage form is in a tablet, capsule or other form, each pulse preferably releases from about 2 to about 15 mg of methylphenidate, more preferably from about 5 to about 10 mg of methylphenidate.

Another preferred active ingredient for use in the dosage forms of the present invention is levodopa, optionally, in combination with an inhibitor of the aromatic L-amino decarboxylase enzyme such as carbidopa. The most preferred mode for treating Parkinson's patients is a formulation where the levodopa and carbidopa are uniformly dispersed in the gastric retention delivery system. A most preferred formulation for the GRDS with levodopa and carbidopa homogeneously mixed in the matrix comprises about 10 wt. % to about 14 wt. % HPMC, from about 42 wt. % to about 47 wt. % HPC, from about 7 wt. % to about 12 wt. % croscarmellose sodium, from about 6 wt. % to about 9 wt. % tannic acid, from about 18 wt. % to about 22 wt. % levodopa, from about 3 wt. % to about 6 wt. % carbidopa, and, optionally, from about 0.3 wt. % to about 1.0 wt. % of a tablet lubricant such as magnesium stearate. This formulation can be administered every 8 hours and is a distinct improvement over current dosing.

A second most preferred mode for treating Parkinson's patients is nighttime dosing of levodopa so that the patient wakes in an "on" state. In this case a slow release tablet of levodopa/carbidopa is embedded in the expanding composition so that a delay of drug release is obtained while the delivery system remains in the stomach. A slow release tablet based on HPMC, for example as is known in the art, is embedded, using a Kilian RUD press coat machine or equivalent, in the expanding composition. The most preferred formulation for this use is from about 10 wt. % to about 20 wt. % HPMC, from about 50 wt. % to about 60 wt. % HPC, from about 12 wt. % to about 25% wt. % croscarmellose sodium, from about 8 wt. % to about 12 wt. % tannic acid and from about 0.5 wt. % to about 1 wt. % tablet lubricant such as magnesium stearate. This tablet would be taken at night before sleep, will delay release until the early morning hours, and will then slowly release the drug.

The levodopa dose is preferably from about 150-250 mg, more preferably about 200 mg, in the most preferred dosage forms for delivery of levodopa, optionally in combination with an amino decarboxylase enzyme inhibitor. When carbidopa is used, the carbidopa dose is preferably from about 25 to about 100 mg, more preferably about 50 mg, in the most preferred dosage forms for delivery of levodopa and an amino decarboxylase enzyme inhibitor.

The dosage forms of the present invention are useful for administration of a wide variety of active ingredients. The dosage forms are particularly valuable for delayed, sustained and pulsed delivery of drugs that have a narrow window of bioavailability due to slow absorption or selective absorption by the stomach, duodenum or jejunum. The dosage forms may be used to administer drugs that are best absorbed through the lining of the stomach, duodenum or jejunum and drugs intended to have a local effect in these regions. Drugs intended to have a local effect in the stomach include antipeptic ulcer drugs, antacids, drugs for treating gastritis and esophagitis, and drugs to reduce risk of gastric carcinoma. As previously discussed, dosage forms made according the present invention have distinct therapeutic advantages for treatment of attention deficit disorder and hyperactivity in children with methylphenidate, treatment of Parkinson's disease with levodopa and treatment of bone loss with alendronate and other bis-phosphonates.

Other active ingredients that may be administered in the drug delivery vehicles of the present invention include adrenergic receptor agonists and antagonists; muscarinic receptor agonists and antagonists; anticholinesterase agents; neuromuscular blocking agents; ganglionic blocking and stimulating agents; sympathomimetic drugs; serotonin receptor agonists and antagonists; central nervous system active drugs such as psychotropic drugs, antipsychotic drugs, antianxiety drugs, antidepressants, antimanic drugs, anesthetics, hypnotics, sedatives, hallucinogenic drugs and antihallucinogenic drugs; antiepileptic drugs; antimigraine drugs; drugs for treatment of Parkinson's, Alzheimer's and Huntington's disease; analgesics; antitussive agents; antihistaminic drugs; $H_1$, $H_2$, and $H_3$ receptor antagonists; bradykinin receptor antagonists; antipyretic agents; antiinflammatory agents; NSAIDs; diuretics; inhibitors of $Na^+$—$Cl^-$ symport; vasopressin receptor agonists and antagonists; ACE inhibitors; angiotensin II receptor antagonists; renin inhibitors; calcium channel blockers; β-adrenergic receptor antagonists; antiplatelet agents; antithrombic agents; antihypertensive agents; vasodialators; phosphodiesterase inhibitors; antiarrhythmic drugs; HMG CoA reductase inhibitors; $H^+$, $K^+$-ATPase inhibitors; prostaglandins and prostaglandin analogs; laxatives; antidiarrheal agents; antiemetic agents; prokinetic agents; antiparasitic agents such as antimalarial agents, antibacterial agents, drugs for treatment of protozoal infections and antihelmintic drugs; antimicrobial drugs such as sulfonamides, quinolones, β-lactam antibiotics, aminoglycosides, tetracyclines, chloramphenicol and erythromycin; drugs for treatment of tuberculosis, drugs for treatment of leprosy; antifungal agents; antiviral agents; immunomodulators; hematopoietic agents; growth factors; vitamins; minerals; anticoagulants; hormones and hormone antagonists such as antithyroid drugs, estrogens, progestins, androgens, adrenocortical steroids and adrenocortical steroid inhibitors; insulin; hypglycemic agents; calcium resorption inhibitors; clucocorticoids; retinoids and heavy-metal antagonists. The active ingredient in the dosage form may be a pharmaceutically acceptable salt, prodrug or derivative of the agent that exerts a therapeutic effect in the patient.

In addition to the above-described excipients, the drug delivery vehicle may further include one or more other excipients that may be added to the vehicle for a variety of purposes. It will be understood by those in the art that some substances serve more than one purpose in a dosage form. For instance, some substances are binders that help hold a tablet together after compression, yet are disintegrants that help break the tablet apart once it reaches a patient's stomach. It will be further understood that the hydrogel, superdisintegrant and tannic acid of the expanding composition may serve to perform additional functions in the dosage form, which functions may already be known to those skilled in the art.

Diluents increase the bulk of a solid pharmaceutical product and may make it easier for the patient and care giver to handle. Diluents include, for example, microcrystalline cellulose (e.g., Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., Eudragit®), potassium chloride, powdered cellulose, sodium chloride, sorbitol and talc.

Compacted dosage forms like those of the present invention may include excipients whose functions include helping to bind the active ingredient and other excipients together after compression. Binders for solid pharmaceutical compositions include, but are not limited to, acacia, alginic acid, carbomer (e.g., carbopol), carboxymethylcellulose sodium, dextrin, ethyl cellulose, gelatin, glucose, guar gum, hydrogenated vegetable oil, hydroxyethyl cellulose, hydroxypropyl cellulose (e.g., Klucel®), hydroxypropyl methylcellulose (e.g., Methocel®), liquid glucose, magnesium aluminum silicate, maltodextrin, methylcellulose, polymethacrylates, polyvinylpyrrolidone (e.g., Kollidon®, Plasdone®), starch, pregelatinized starch, sodium alginate and alginate derivatives.

The dissolution rate of a compacted dosage form in the patient's stomach also may be adjusted by the addition of a disintegrant or second superdistegrant to the dosage form, in addition to the superdisintegrant of the present inventive composition. Such additional disintegrants include, but are not limited to, alginic acid, carboxymethylcellulose calcium, carboxymethylcellulose sodium (e.g., Ac-Di-Sol®, Primellose®), colloidal silicon dioxide, croscarmellose sodium, crospovidone (e.g., Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g., Explotab®) and starch.

Glidants can be added to improve the flow properties of a solid composition and improve the accuracy of dosing. Excipients that may function as glidants include, but are not limited to, colloidal silicon dioxide, magnesium trisilicate, powdered cellulose, starch, talc and tribasic calcium phosphate.

When a dosage form such as a tablet is made by compaction, a composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease release of the product from the dye. Lubricants include, but are not limited to, magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, surfactants, talc, waxes and zinc stearate.

Flavoring agents and flavor enhancers make the dosage form more palatable to the patient. Common flavoring agents and flavor enhancers for pharmaceutical products that may be included in the drug delivery vehicle of the present invention include, but are not limited to, maltol, vanillin, ethyl vanillin, menthol, citric acid, fumaric acid ethyl maltol, and tartaric acid.

The dosage forms may also be colored using any pharmaceutically acceptable colorant to improve their appearance and/or facilitate patient identification of the product and unit dosage level.

Having thus described the present invention with reference to certain preferred embodiments, the following examples are provided to further illustrate the invention.

EXAMPLES

Materials

The HPMC used was Methocel® K-15PM, available from Dow Chemical Co. The hydroxypropyl cellulose used was Klucel® HF NF, available from Hercules, except where otherwise indicated. The croscarmellose sodium used was Ac-Di-Sol® available from Avebe Corp. The crosslinked polyacrylic acid was Carbopol® 974P available from B. F. Goodrich Chemical Ltd. Tannic Acid was purchased from Merck. All materials were pharmaceutical grade.

Example 1

Preparation of Tablets

The compositions of each of the tablets prepared in Example 1 are summarized in Table 1. All the compositions contain hydroxypropyl methylcellulose, tannic acid, a superdisintegrant and 1% magnesium stearate. All of the excipients, except for magnesium stearate, were mixed simultaneously and thoroughly blended by hand. Magnesium stearate was then added at a level of 1% w/w and the blend was further mixed by hand until the magnesium stearate was uniformly distributed throughout the composition. The amount of each composition needed to produce a 5 mm thick tablet was determined and then that amount was compressed into 5 mm thick tablets on a Manesty f3 single punch tableting machine with a 10 mm diameter punch and die. Tablets ranged in weight from 350-400 mg and each had a hardness within the range of 5-7 KP as tested in an Erweka hardness tester.

Expansion Tests

The tablets were added to 40 ml of simulated gastric fluid (0.1M HCl) contained in a 50 ml beaker and maintained at 37±2° C. The tablets were removed after fifteen minutes with a tweezers and measured with a caliper. Gel strength was assessed qualitatively with the tweezers.

The results of the expanding tests are summarized in Table 2. Expansion of the hydrogel was enhanced using either croscarmellose sodium or sodium starch glycolate. The formulation can optionally and advantageously contain a mixture of two hydrogel polymers as demonstrated by the incorporation hydroxypropyl cellulose and Carbopol® in the formulations of Examples 5, 6 and 8. The tablet that expanded the most (36 fold) contained about 5 wt. % tannic acid and croscarmellose sodium as the superdisintegrant. The tablet with the second highest expansion (18 fold) also contained about 5 wt. % tannic acid but used sodium starch glycolate as the superdisintegrant. Both of those gels (Examples 1 and 4) were qualitatively weak compared to those of examples 5-8. The best performing tablets in terms of a high degree of expansion and good mechanical strength are those of Examples 5 and 8, which contained 5 wt. % tannic acid and used both hydroxypropyl methylcellulose and hydroxypropyl cellulose hydrogel polymers.

TABLE 2

| Formulation No. | Degree of Expansion[a] | Strength |
|---|---|---|
| 1 | 18.1 | moderate |
| 2 | 12.7 | moderate |
| 3 | 7.2 | moderate |
| 4 | 36.0 | moderate |
| 5 | 10.4 | strong |
| 6 | 2.0 | strong |
| 7 | 4.5 | strong |
| 8 | 9.7 | strong |

[a]ratio of hydrated tablet volume to dry tablet volume

Example 2

Rate and Degree of Swelling of Placebo Formulations

The formulations in Table 3, below, were prepared by first dry mixing the powdered ingredients, except the magnesium stearate, for 5 minutes. Magnesium stearate was then added and blended in over 2 minutes. The formulation was pressed into oval tablets of dimensions 17×9×8.5 mm using a Manesty f3 single punch tablet press where the 8.5 is the tablet thickness or height in the dimension of compression.

TABLE 1

| | Formulation No. (wt. %) | | | | | | | |
|---|---|---|---|---|---|---|---|---|
| Excipient | 1 | 2 | 3 | 4 | 5 | 6 | 7 | 8 |
| Hydroxypropyl methylcellulose | 23.8 | 32.7 | 30.3 | 23.8 | 26.7 | 38.5 | 34.8 | 15.9 |
| Hydroxypropyl cellulose | 0.0 | 0.0 | 0.0 | 0.0 | 16.0 | 19.2 | 0.0 | 47.6 |
| Cross-linked polyacrylic acid | 0.0 | 0.0 | 0.0 | 0.0 | 0.0 | 0.0 | 8.7 | 0.0 |
| Total hydrogel | 23.8 | 32.7 | 30.3 | 23.8 | 42.7 | 57.7 | 43.5 | 63.5 |
| Sodium starch glycolate | 71.4 | 65.4 | 60.6 | 0.0 | 53.3 | 38.5 | 52.2 | 31.7 |
| Croscarmellose sodium | 0.0 | 0.0 | 0.0 | 71.4 | 0.0 | 0.0 | 0.0 | 0.0 |
| Tannic acid | 4.8 | 2.0 | 9.1 | 4.8 | 4.0 | 3.8 | 4.3 | 4.8 |
| Total | 100 | 100 | 100 | 100 | 100 | 100 | 100 | 100 |

TABLE 3

Formulations of Placebo GRDS

| Ingredient | Formulation No. (wt. %) | | |
|---|---|---|---|
| | 10 | 11 | 12 |
| HPMC K15 | 16 | 15.7 | 13.4 |
| HPC | 48 | 47.2 | 45 |
| Croscarmellose sodium | 31.9 | 31.4 | 29.1 |
| Tannic acid | 3.1 | 4.7 | 12 |
| Magnesium stearate | 1 | 1 | 0.5 |

The tablets were immersed in 450 ml of USP Gastric TS buffer (pH=1.2) without enzymes at 37° C. in a USP type II dissolution bath with the paddles set at the top of the buffer so as not to hit the expanding tablets. The solution was stirred at 50 RPM. The tablets were removed from the buffer at 15 minutes, 1 and 3 hours, gently blotted dry with paper, and measured using a calibrated caliper. The two major dimensions, length and height, were measured. The third dimension expanded from 9 mm to about 14 mm in all of the cases. Results of the measurements are shown in Table 4.

TABLE 4

Expansion of the Placebo GRDS tablets in USP Gastric TS buffer

| | Formulation No.: | | |
|---|---|---|---|
| Time (hours) | 10 Size (mm × mm) | 11 Size (mm × mm) | 12 Size (mm × mm) |
| 0 | 17 × 8.5 | 17 × 8.5 | 17 × 8.5 |
| 0.25 | 21 × 15 | 25 × 21 | 25 × 18 |
| 1 | 21 × 15 | 32 × 24 | 27 × 19 |
| 3 | 21 × 15 | 32 × 24 | 27 × 20 |

Most of the expansion occurred in the first 15 minutes. One can see that the degree of expansion was greatest in the dimension of compression. This dimension expanded between 1.8 and 2.8 times its size. In length, the tablet grew from 1.2 to 1.9 times its size.

Example 3

Method

Gel strength was measured by the weight needed to deflect the expanded gel by 4 mm. The gels were removed from the Gastric TS buffer, blotted dry with paper, and placed on a flat surface on a top loading balance. A plastic cylinder was placed on the gel and water was added slowly to the cylinder until the gel was compressed downward by 4 mm. The weight required for 4 mm deflection was recorded.

Effect of Tannic Acid Content on Gel Strength

Formulations were prepared as in Example 2 with varying amounts of tannic acid. Tablets were pressed and immersed in simulated gastric fluid as described in Example 2. All the tablets swelled to at least 25×22 mm in 15 minutes. Results of the measurement of gel strength are found in Table 5.

TABLE 5

Strength of Expanded Gels as a Function of Tannic Acid Content

| Formulation | % Tannic Acid | Strength (g) |
|---|---|---|
| 13 | 4.2 | 27 |
| 14 | 4.7 | 51 |
| 15 | 6 | 90 |
| 16 | 7 | 147 |

Raising the percent of tannic acid from 4.2 to 7 percent dramatically increased the strength the expanded gel. In experiments not reported in Table 5 it was discovered that increasing the percent of tannic acid from 7 and 12% resulted in little further increase in gel strength.

Effect of Superdisintegrant Content on Gel Strength

Formulations were prepared as described in Example 2 with varying amounts of croscarmellose sodium. Tablets were pressed and the tablets were immersed in simulated gastric fluid as described in Example 2. All the tablets swelled to at least 23×18 mm in 15 minutes. The formulations tested and the results of the measurement of gel strength are provided in Table 6.

TABLE 6

Strength of Expanded Gels as a Function of Croscarmellose Sodium Content

| Ingredient | Formulation No. (wt. %) | | |
|---|---|---|---|
| | 17 | 18 | 19 |
| HPC | 46.6 | 50 | 55.9 |
| Croscarmellose sodium | 31 | 26 | 21.4 |
| HPMC K15 | 15.5 | 15 | 15.7 |
| Tannic acid | 5.9 | 6 | 6 |
| Magnesium stearate | 1 | 1 | 1 |
| Weight required to deflect gel by 4 mm (g) | 90 | 116 | 157 |

As can be seen in Table 6, lowering the percent of the superdisintegrant in the formulation tended to increase the gel strength.

Example 4

Strength of Expanded Gel of Tablets Containing Levodopa/Carbidopa

The formulations in Table 7, containing 200 mg levodopa and 50 mg carbidopa, were prepared as follows. Drug granulate: a solution of 0.75% w/v Klucel LF in ethanol was used as a binding solution for a mixture of 4:1 levodopa:carbidopa. The granulation was carried out in a Zanchetta Rotolab one pot granulator. The granulate was either dried under vacuum in the granulator or air dried at room temperature protected from light. The final composition of the granulate was levodopa 80.5%, Carbidopa 19.9%, Klucel LF 0.6%. A drug granulate containing levodopa was prepared by the same method. Final composition: 99.4% levodopa, 0.6% Klucel LF.

The dried granulate was milled through a 0.63 mm sieve and then mixed with the other powders and tablets pressed as described in Example 2. The drug granulate was dispersed uniformly throughout the expanding composition. The tablets were swelled and the strength measured as in Example 3. All the formulations swelled to at least 25×22 mm in 15 minutes.

The formulations tested and the strength of the expanded gel measured are given in Table 7.

TABLE 7

Strength of Expanded Gels as a Function of Croscarmellose Sodium Content for Levodopa/Carbidopa GRDS Formulations

| | Formulation (wt. %) | | | | |
|---|---|---|---|---|---|
| Ingredient | 20 | 21 | 22 | 23 | 24 |
| HPMC | 12.7 | 12.7 | 17.7 | 12.7 | 13.4 |
| HPC | 38.4 | 43.4 | 38.4 | 45.9 | 48.4 |
| Croscarmellose sodium | 16.8 | 11.8 | 11.8 | 9.3 | 9.8 |
| Tannic acid | 7.6 | 7.6 | 7.6 | 7.6 | 8 |
| Levodopa/carbidopa granulate | 24.1 | 24.1 | 24.1 | 24.1 | — |
| Levodopa granulate | — | — | — | — | 20 |
| Magnesium stearate | 0.4 | 0.4 | 0.4 | 0.4 | 0.4 |
| Weight required to deflect gel by 4 mm (g) | 100 | 162 | 168 | 282 | 298 |

As can be seen in Table 7, lowering the superdisntegrant content of the formulation has a strong influence on tablet strength as was found with the placebo formulations. Whether the amount of croscarmellose was replaced with HPC as in Formulation No. 21 or with HPMC as in Formulation No. 22 had no effect on the gel strength.

Example 5

Release of Drugs Homogeneously Dispersed in the GRDS Formulation

Formulations of different drugs, or drug granulates, were prepared by direct compression techniques where the drug is uniformly dispersed in the powder mixture and tablets were pressed as described in the previous examples. The release of the drug was measured in 900 ml USP Gastric TS in a USP type II dissolution apparatus at 37° C. and 50 RPM with the paddle in the standard position. The swollen tablets, which were of neutral density, were occasionally hit by the paddle during the release experiments. The tablets were strong enough not to be deformed by such battering.

Levodopa and Carbidopa Tablets

The release of the drugs from Formulations 23 and 24 described above in Example 4 was measured. The cumulative amount of drug released was measured by HPLC using the following conditions:
 Column: Merck Lichrosphere 60 RP-Select B Sym 125×4 mm
 Mobile phase: 94:4 Phosphate buffer (pH=2.3):Acetonitrile
 Flow rate: 1 ml/min
 Detector: UV at 280 nm
 Retention times: Levodopa 5 minutes; Carbidopa 13 minutes Levodopa and carbidopa are released from the GRDS system at about the same rate of ~8%/hour. Formulations 23 and 24 afford an extended controlled release of the two drugs. The release rate data is provided in Table 8.

TABLE 8

Cumulative Release of Levodopa and Carbidopa Homogeneously Dispersed in the GRDS

| | Formulation No.: | | |
|---|---|---|---|
| | 23 | | 24 |
| Time (h) | Levodopa (%) | Carbidopa (%) | Levodopa (%) |
| 1 | 9 | 8.5 | 11.4 |
| 2 | 21.4 | 18.1 | 26.1 |
| 3 | 30.8 | 26.4 | 33 |
| 4 | 37.6 | 33.4 | 39.1 |
| 5 | 44.5 | 39.6 | — |
| 6 | 52.8 | 53.5 | 48.8 |
| 7 | 58.1 | 56.9 | — |
| 8 | 64 | 62 | 54.6 |
| 12 | — | — | 67.9 |
| 18 | — | — | 78.5 |
| 24 | — | — | 92.4 |

Acetaminophen Tablets

Diffused tablets of acetaminophen at dose levels of 200 mg and 10 mg per tablet were prepared with the tablet weight being 1 gram. The formulations are given in Table 9.

TABLE 9

Formulations of GRDS with Acetaminophen Homogeneously Dispersed in the Tablet

| | Formulation (wt. %) | |
|---|---|---|
| Ingredient | 25 | 26 |
| HPMC | 16.7 | 13 |
| HPC | 56.3 | 46 |
| Croscarmellose sodium | 15 | 10 |
| Tannic acid | 1 | 10 |
| Acetaminophen | 1 | 20 |
| Magnesium stearate | 1 | 1 |

The release of the drug was measured in Gastric TS as described above and the cumulative drug release measured by HPLC using the following conditions:
 Column: Hypersyl ODS 250×4.6 mm, 5 micron
 Mobile phase: 75:25 water:methanol
 Flow rate: 1.5 ml min
 Detector: UV at 243 nm
 Retention times: 3.5 minutes The results of the drug release are shown in Table 10. One sees an extended controlled release of this soluble drug.

TABLE 10

Cumulative Release of Acetaminophen Homogeneously Dispersed in the GRDS

| | Percent Release | |
|---|---|---|
| Time (h) | 25 | 26 |
| 1 | 11.8 | 16.0 |
| 2 | 20.2 | 25.0 |
| 3 | 28.0 | 32.6 |
| 4 | 34.9 | 39.2 |
| 20 | 86.1 | 91.5 |

Alendronate Tablets

Sodium Alendronate monohydrate was dispersed in the GRDS tablet at a weight equivalent to 10 mg alendronic acid per tablet. The formulation is given in Table 11 and the release profile in Table 12. Alendronate concentrations were measured using HPLC on the FMOC (9-Fluroneylmethylchloroformate) derivative using the following conditions:

Column: Hamilton PRP-1,250×4.1 mm, 5 micron

Mobile phase: 75:20:5 Citrate+Phosphate buffer (pH=8): Acetonitrile:methanol

Flow rate: 1.0 ml/min

Detector: UV at 266 nm

Retention time: 5.6 minutes

TABLE 11

Formulation of Alendronate Homogeneously Dispersed in the GRDS

| Ingredient | Formulation No. 27 (wt. %) |
|---|---|
| HPMC | 16.7 |
| HPC | 56.6 |
| Croscarmellose sodium | 14 |
| Tannic acid | 10 |
| Sodium alendronate monohydrate | 1.67 |
| Magnesium stearate | 1 |

TABLE 12

Cumulative Release of Alendronate Homogeneously Dispersed in the GRDS

| Time (h) | % Release |
|---|---|
| 1 | 2.5 |
| 2 | 3.1 |
| 3 | 5 |
| 5 | 7 |
| 8 | 12.6 |
| 24 | 45 |

Example 6

Release of Levodopa and Carbidopa from an Embedded Reservoir in the GRDS

A 275 mg reservoir tablet containing 200 mg levodopa and 50 mg carbidopa unformly dispersed in an HPC matrix was formed. This reservoir slowly erodes to release the drugs over about two hours. This reservoir was embedded in 725 mg of the GRDS formulation of Table 13 and compressed into an oval tablet of dimensions 17×9×8.5 mm.

TABLE 13

| Ingredient | Formulation No. 28 (wt. %) |
|---|---|
| HPC | 50.3 |
| HPMC | 16.7 |
| Croscarmellose sodium | 22 |
| Tannic acid | 10 |
| Magnesium stearate | 1 |

The cumulative release of the two drugs, measured as above in Example 5, is given in Table 14.

TABLE 14

Cumulative Release of Levodopa and Carbidopa from a tablet Embedded in the GRDS

| Time (h) | Levodopa (%) | Carbidopa (%) |
|---|---|---|
| 1 | 1.1 | 0.9 |
| 2 | 2 | 1.5 |
| 3 | 3.1 | 3 |
| 4 | 5.1 | 5.9 |
| 5 | 16.4 | 16.9 |
| 6 | 69.7 | 73.7 |

Both drugs show an initial delay in release followed, several hours later, by the two drugs being released in parallel. The inner eroding tablet was designed for a short controlled release. This example shows the feasibility of giving the GRDS levodopa/carbidopa at night for a delayed delivery in the stomach in the early morning. This tablet also could be designed to give a more extended release profile.

Release of Alendronate from a Reservoir Partially Embedded in the GRDS

Two different formulations of an inner tablet of alendronate, Formulations 29 and 30, were prepared and embedded in the GRDS formulation such that one face of the embedded tablet was partially exposed to the surface. The GRDS formulation used was:

TABLE 15

| Ingredient | GRDS of Formulations Nos. 29 & 30 (wt. %) |
|---|---|
| HPC | 57.3 |
| HPMC | 16.7 |
| Croscarmellose sodium | 15 |
| Tannic acid | 10 |
| Magnesium stearate | 1 |

The inner core for Formulation No. 29 was formed by wet granulation of sodium alendronate monohydrate and urea with 50% aqueous ethanol, drying, milling and mixing the powder with magnesium stearate. The tablets pressed were of 5 mm diameter, weighed 50 mg/tablet and contained 11.6 mg of the sodium alendronate monohydrate, 37.9 mg urea and 0.5 mg magnesium stearate per tablet.

The inner core of Formulation No. 30 was formed by mixing the alendronate salt and Avicel, adding magnesium stearate and mixing for a few minutes and again pressing 50 mg tablets of 5 mm diameter that contain 11.6 mg sodium alendronate monohydrate, 37.9 mg Avicel and 0.5 mg magnesium stearate per tablet.

The release of alendronate was measured as described in Example 5 and the results of those measurements are provided in Table 16. As can be seen from the cumulative release over 21 h, partially embedded tablets are another means of achieving extended controlled release from the GRDS system in a patient's stomach.

TABLE 16

Cumulative Release of Alendronate
from Partially Embedded Tablets

| | Cumulative Percent Release | |
|---|---|---|
| Time (h) | Form. 29 | Form. 30 |
| 1 | 16 | 7 |
| 2 | 23.7 | 18 |
| 3 | 27.8 | 31 |
| 4 | 31.6 | 41 |
| 6 | 44.2 | 53 |
| 21 | 79.6 | — |

Example 7

In Vivo Release of Levodopa/Carbidopa in a Beagle Dog

Levodopa, the mainstay of treatment for Parkinson's disease, would benefit from an extended drug release profile. However, conventional extended release formulations cannot be used for this drug because it is absorbed in the duodenum only and not in the distal small intestine nor in the colon. The residence time of a drug in the duodenum is very short, on the order of minutes. Any extended delivery of levodopa must be in the stomach from where the drug will transfer to the duodenum, its site of absorption. Therefore, a gastric retention extended delivery vehicle will greatly enhance levodopa's efficacy in treating Parkinson's disease. The drug is also an excellent indicator of gastric retention. Shortly after gastric emptying the drug is no longer absorbed. Levodopa also has a short half life in the blood. All extended absorption found in an in vivo trial is indicative of gastric retention with duodenal absorption.

Methods

Blood Sampling for Pharmacokinetic Evaluation

Prior to the study, an adequate amount (5-10 ml) of whole blood was drawn from the dog to prepare a standard calibration reference curve.

In addition, four labeled Eppendorf microcentrifuge tubes were prepared for each sampling time (i.e., hourly intervals from 0-12 hours). To each of the prepared microcentrifuge tubes was added 50 µL of water plus 300 µL of an extraction mixture. The extraction mixture consists of 25.5 ml 70% perchloric acid, 2.5 grams sodium metabisulfite, 2.5 grams sodium lauryl sulfate, 0.25 grams disodium EDTA, 2.5 ml TEA, 50 ml Ethanediol, and 1.25 grams Tween 20, up to a total volume of 500 ml, adjusting to volume with water.

At the study, the foreleg (right or left, as deemed appropriate by the animal handler), was shaved using an electric shaver, and the area cleansed with a chlorhexidine swab. A permanent in-dwelling polyethylene catheter using a 23 gauge needle was inserted in the cephalic vein in the foreleg of each dog and taped in place to allow for periodic blood sampling over 12 hours. A plastic bonnet was placed around the head of each dog to ensure that the dog's mouth could not reach the catheter site.

At each time point, 2.0 ml blood was removed by syringe and then placed into the pre-labeled heparinized test tube. The test-tube, was shaken vigorously by hand. Then, four aliquots, each containing 250 µL of whole blood, were withdrawn from the test-tube by pipette and immediately added to one of the four labeled Eppendorf microcentrifuge tubes, for that sampling time point.

The Eppendorf microcentrifuge tubes were vortexed and then immediately transferred to a deep freezer where the samples were maintained at −70° C.

The aliquot tubes were weighed and 25 µL of 1M $Na_2HPO_4$ solution containing $Na_2S_2O_5$ (10% w/v) were added to the tubes. The tubes were then centrifuged at 13000 g for about 15 minutes at 4° C. The supernatant from each sample was filtered through a 0.2 µm syringe filter. The residual supernatants were stored frozen at −70° C. in labeled vials in case sample dilution was required.

HPLC Analysis

The levels of levodopa and carbidopa in whole blood were determined by reversed phase high performance liquid chromatography (RP-HPLC) with electrochemical detection.

The HPLC column was a Licrosphere 60RP select B, 5 µm, 250×4.0 mm, (Merck, #1.50214) with a Licrocart 4-4 cartridge 60RP select B, 5 µm, 4.0×4.0 mm (Merck, No. 1.50963). The injection volume was 10 µl, with a sample temperature of 5° C. and a flow rate of 1.3 ml/min.$^{-1}$; The column temperature was 50° C., with a run time of about 10 minutes. The electrochemical detector (Coulochem II 5200-A ESA Huntingdon, UK, Model 5010; Analytical Cell=Model 5021) had the following parameters: Potential $E_1$=−350 mV; Potential $E_2$=+250 mV; Guard Potential E=−50 mV; Rise Time −5 seconds, and Gain −1 µA.

The lower limits of detection (LLD) for both levodopa and carbidopa were 12.5 ng/ml.

The Study

The dog was fasted overnight for a period of at least 12 hours at which time he received a single mixed meal of solid food and liquid nutrients. 250 grams of bite-size commercial dog chow (Bonzo Feed) were measured and placed in a feeding dish. The dog was allowed to eat over ½ hour, at which time the dish was removed. The food remaining in the dish was measured and the difference from the original 250 grams was recorded as the amount of food consumed. Additionally, 250 calories of liquid nutrients (Ensure®, 237 ml) were administered via a gastroesophageal feeding tube. No additional food was allowed for the duration of the study, but water was provided ad libitum from a tap in the dog's cage during the study.

Within two hours following the meal, the dog was prepared for catheter insertion and a "pre-dosing" "0" hour blood sample was drawn. The blood was drawn and the sample handled as described above ("Blood Sampling for Pharmacokinetic Evaluation").

Two hours after the meal, after the "pre-dosing" blood sample was taken, the dog was dosed with Formulation 23 (Example 4, Table 7) with the following composition:

| | Formulation 23 | |
|---|---|---|
| Ingredient | wt. % | wt. (mg) |
| HPMC | 12.7 | 132 |
| HPC | 45.9 | 476 |
| Croscarmellose sodium | 9.3 | 96 |
| Tannic acid | 7.6 | 79 |
| Levodopa | 19.3 | 200 |
| Carbidopa | 4.8 | 50 |
| Magnesium stearate | 0.4 | 4 |
| Total | 100 | 1037 |

After administering the test hydrogel, 300 mg of pH regulated (pH of 2.0) water was administered, via flexible tubing to the stomach.

Every hour following dosing, up to 12 hours, a blood sample (2 ml) of whole blood was withdrawn from the catheter and placed in a heparinized glass test-tube, from which 4 individual aliquots (250 µl) were removed and each aliquot placed into a labeled, prepared Eppendorf microcentrifuge tube. The microcentrifuge tubes were vortexed (Vortex-2 Genie; Scientific Industries Model G-560E) for a few seconds and then immediately placed in a deep freezer, where the samples were maintained at −70° C. until analysis.

For each sampling time, four aliquots were prepared and frozen. Replicate samples were assayed over the next few days for levodopa and carbidopa levels, while the remaining two aliquots were stored in the deep freezer for future analysis.

Results

The Results of the vivo release of levodopa/carbidopa are shown in Table 17.

TABLE 17

In Vivo Release of Levodopa/Carbidopa in a Beagle Dog

| Time (h) | Blood Concentration (ng ml$^{-1}$) | |
|---|---|---|
| | Levodopa | Carbidopa |
| 0 | 0.0 | 0 |
| 1 | 96.5 | 0 |
| 2 | 104.1 | 32.5 |
| 3 | 574.3 | 52.8 |
| 4 | 653.1 | 86.3 |
| 5 | 387.4 | 75.0 |
| 6 | 1008.7 | 119.2 |
| 7 | 1934.8 | 337.0 |
| 8 | 1783.1 | 661.8 |
| 9 | 371.1 | 226.7 |
| 10 | 214.0 | 145.7 |
| 11 | 202.3 | 174.0 |
| 12 | 96.5 | 70.9 |

The release of the two drugs is delayed and quite extended. There are significant levels of levodopa for at least 6 hours and the peak is delayed, indicating that the delivery system was in the stomach for many hours releasing the drugs. The data of Table 17 is FIG. 1.

Example 8

Gastric Retention delivery System with In Situ External Tablet Adhesion

One method of obtaining pulsed delivery of a drug in the stomach is to attach tablets with predetermined delays before disintegration to the gastric retention delivery system (GRDS) table. Such attachment can be through partial embedding of the tablet in the GRDS matrix of by adhering it externally to the GRDS. In this example we show the feasibility of such external adhesion.

The GRDS formulation was that shown in Table 13 of Example 6. The powders, except the lubricant, were mixed for five minutes. Magnesium stearate was then added and the powders mixed for one minute more. The blend was pressed into rectangular (truncated oval) tablets of 10×7×7 mm in a Manesty f3 single punch tableting machine.

An adhesive solution was prepared as follows. Sodium caseinate (Emolac™ 50, 15 g) was dissolved in 100 ml water by stirring overnight at room temperature. 500 ml of ethanol was added with stirring to obtain an emulsion of 2.5% sodium caseinate in water:ethanol.

The tablets were then coated with the adhesive. The emulsion was spray coated on the tablets in a pan coater at a rate of 4 ml/min with the product temperature between 30-40° C. to a coating weight of between 5 and 14 mg. The tablets were air dried in the coating pan to give GRDS tablets coated with the adhesive.

Placebo tablets based on microcrystalline cellulose were prepared (5×5×5 mm rectangular) and coated with Eudragit™ S to make them impervious to acid conditions. The tablets were loaded into a gelatin #00 capsule in a stack such that a GRDS tablet was in between two placebo tablets. The contact between the tablets was on the 7×7 mm face of the GRDS tablet which is perpendicular to the compression axis.

The gelatin capsules were placed in 0.1 N HCl in a USP type II dissolution bath at 37° C. and stirred at 50 RPM. The capsule dissolved and the three tablet stack adhered to one another in situ. Within 15 minutes the GRDS tablet had swollen to 13×22 mm from 10×7 mm (the swelling being mostly along the compression axis). At two hours the GRDS tablet had swollen to 14×25 mm. The placebo tablets remained attached to the GRDS tablet, despite its swelling, for over 12 hours in the dissolution bath. In order to test the viability of the adherence under more vigorous conditions of flow, the stack was placed in 0.1 N HCl at 37° C. in a disintegration tester at 50 strokes per minute. The flows on the tablets in a disintegration tester are considerably stronger than in the dissolution tester. The three tablets remained adhered to one another for 10 hours.

Example 9

Timed Pulsed Delivery of Methylphenidate

Methylphenidate disintegrating tablets of the formulation shown in Table 18 were prepared.

TABLE 18

| Ingredient | Percent |
|---|---|
| Methylphenidate | 10 |
| HPC (Klucel LF) | 5 |
| Starch | 25 |
| Microcrystalline cellulose (Avicel) | 49 |
| Sodium starch glycolate | 10 |
| Magnesium stearate | 1 |

The preparation of the tablets was as follows. Two parts methylphenidate were granulated with one part HPC and five parts starch by adding two parts water and mixing in a Zanchetta Rotolab one pot granulator. The granulate was dried in a fluidized bed drier at 45° C., and milled through a 0.63 mm sieve. The granulate was mixed with microcrystalline cellulose and sodium starch glycolate for five minutes, magnesium stearate added and the mixing continued for 1 minute. The blend was pressed into 5 mm tablets of 100 mg each in a Manesty f3 single punch tableting machine.

A coating solution was prepared by dissolving 5 grams of ethylcellulose, 0.75 grams urea, and 0.5 grams triethylcitrate in ethanol for a total weight of 100 grams. This solution was sprayed on the tablets in a pan coater with the tablet bed kept at 30-40° C. Different weights of coating were sprayed on the tablets. The tablets were tested for delay in burst drug release in a USP type II dissolution apparatus in 0.1N HCl at 37° C.

and 50 RPM. The results of the burst delay as a function of coating level is shown in Table 19.

TABLE 19

| Coating level (mg/tablet) | Burst Time (h) |
|---|---|
| 4 | 2 |
| 6 | 5 |
| 8 | 12 |

Tablets of this type can be adhered to GRDS tablets to afford extended residence in the stomach and burst release of methylphenidate.

Having thus described the invention with reference to certain preferred embodiments, other embodiments will become apparent to one skilled in the art from consideration of the specification and examples. It is intended that the specification, including the examples, is exemplary only, with the scope and spirit of the invention being defined by the claims which follow.

What is claimed is:

1. A pharmaceutical dosage form for oral administration to a patient providing pulsed gastric release of methylphenidate comprising:
    a) a gastric retention vehicle composition comprising about 10 wt-% to about 75 wt-% superdisintegrant, about 2 wt-% to about 12 wt-% tannic acid, and about 20 to about 70 wt-% of a hydrogel, whereby the gastric retention vehicle composition is a homogenous solid matrix and the percentages are calculated with respect to the matrix exclusive of other excipients and the methylphenidate,
    b) a plurality of first particles containing methylphenidate that are dispersed in the matrix, wherein the methylphenidate is released from the first particles into the stomach upon contact with gastric fluid, and
    c) a plurality of second particles containing methylphenidate that are dispersed in the matrix, wherein each of the second particles is coated with a coating that is impermeable to methylphenidate and dissolves in gastric fluid, and, after a sufficient amount of the coating is dissolved, the methylphenidate is released from the second particles into the stomach,
    wherein, upon contact with gastric fluid the gastric retention vehicle composition expands to a sufficient degree such that the dosage form is retained in the stomach at least until methylphenidate is released from the second particles.

2. A pharmaceutical dosage form of claim 1 further comprising a plurality of third particles containing methylphenidate that are dispersed in the matrix, wherein each of the third particles is coated with a coating that is impermeable to the methylphenidate and dissolves in gastric fluid and the methylphenidate is released from the third particles into the stomach after the methylphenidate is released from the second particles.

3. The pharmaceutical dosage form of claim 2, wherein the methylphenidate is released from the third particles into the stomach about 3 to about 5 hours after the methylphenidate is released from the second particles.

4. A pharmaceutical dosage form of claim 1 wherein the first particles are coated with a coating that delays release of the methylphenidate from said first particles, with the proviso that the first particles and the second particles are not released at the same time.

5. The pharmaceutical dosage form of claim 1, wherein the methylphenidate is released from the second particles into the stomach about 3 to about 5 hours after administration.

6. A method of treating hyperactivity or attention deficit disorder comprising administering a therapeutically effective amount of methylphenidate in the pharmaceutical dosage form of claim 1 to a patient in need thereof.

7. The pharmaceutical dosage form of claim 1, wherein the coating comprises a film coating agent selected from the group consisting of water soluble resins, water insoluble resins, waxes, lipids, and enteric resins.

8. The pharmaceutical dosage form of claim 1, wherein the superdisintegrant is selected from the group consisting of cross-linked carboxymethylcellulose sodium, sodium starch glycolate, and cross-linked polyvinyl pyrollidone.

9. The pharmaceutical dosage form of claim 1, wherein the hydrogel is hydroxypropyl methyl cellulose or a mixture of hydroxypropyl methyl cellulose and hydroxypropyl cellulose or a cross-linked acrylate polymer.

10. The pharmaceutical dosage form of claim 1, comprising from about 10 wt. % to about 30 wt. % hydroxypropyl methylcellulose, from about 40 wt. % to about 60 wt. % hydroxypropyl cellulose, and about 4 wt. % to about 12 wt. % tannic acid.

11. The pharmaceutical dosage form of claim 1, comprising from about 10 wt. % to about 20 wt. % hydroxypropyl methylcellulose, from about 45 wt. % to about 50 wt. % hydroxypropyl cellulose, and about 4 wt. % to about 6 wt. % tannic acid.

12. A pharmaceutical dosage form for oral administration to a patient providing pulsed gastric release of methylphenidate comprising:
    a) a gastric retention vehicle composition comprising about 20 wt-% to about 70 wt-% of a hydrogel, about 10 wt-% to about 75 wt-% superdisintegrant and about 2 wt-% to about 12 wt-% tannic acid, the percentages calculated exclusive of other excipients or the methylphenidate,
    b) a first reservoir containing methylphenidate embedded in said gastric retention vehicle composition wherein methylphenidate is released from the first reservoir into the stomach upon contact of the dosage form with gastric fluid, and
    c) a second reservoir containing methylphenidate embedded in said gastric retention vehicle composition, wherein the second reservoir is coated with a coating that is impermeable to methylphenidate and dissolves in gastric fluid, and, after a sufficient amount of the coating is dissolved, the methylphenidate is released from the second reservoir into the stomach, wherein, upon contact with gastric fluid the gastric retention vehicle composition expands to a sufficient degree such that the dosage form is retained in the stomach at least until methylphenidate is released from the second reservoir.

13. A pharmaceutical dosage form of claim 12 further comprising a third reservoir containing methylphenidate coated with a coating that is impermeable to methylphenidate and dissolves in gastric fluid, wherein the methylphenidate is released from the third reservoir into the stomach after the methylphenidate is released from the second reservoir.

14. A pharmaceutical dosage form of claim 12 wherein the first reservoir is coated with a coating that delays release of the methylphenidate from said first reservoir.

15. A pharmaceutical dosage form of claim 12 wherein the gastric retention vehicle composition and the reservoirs are encapsulated.

16. The pharmaceutical dosage form of claim 12, wherein the methylphenidate is released from the second reservoir about 3 to about 5 hours after administration.

17. A method of treating hyperactivity or attention deficit disorder comprising administering a therapeutically effective amount of methylphenidate in the pharmaceutical dosage form of claim 12 to a patient in need thereof.

18. The pharmaceutical dosage form of claim 12, wherein the coating comprises polymethacrylate, or a mixture of hydrophilic and hydrophobic film forming agents.

19. The pharmaceutical dosage form of claim 18, wherein the hydrophilic film forming agent is selected from the group consisting of methyl cellulose, hydroxypropyl methylcellulose, cellulose phthalate, cellulose acetate phthalate, and polyvinyl alcohol.

20. The pharmaceutical dosage form of claim 18, wherein the hydrophobic film forming agent is selected from the group consisting of ethyl cellulose, cellulose acetate, hydroxypropyl methylcellulose phthalate, polyvinyl alcohol maleic anhydride copolymers, β-pinen polymers rosin, partially hydrogenated rosin, and glycerol esters of rosin.

21. The pharmaceutical dosage form of claim 12, wherein the superdisintegrant is selected from the group consisting of cross-linked carboxymethylcellulose sodium, sodium starch glycolate, and cross-linked polyvinyl pyrollidone.

22. The pharmaceutical dosage form of claim 12, wherein the hydrogel is hydroxypropyl methyl cellulose or a mixture of hydroxypropyl methyl cellulose and hydroxypropyl cellulose or a cross-linked acrylate polymer.

23. The pharmaceutical dosage form of claim 12, comprising from about 10 wt. % to about 30 wt. % hydroxypropyl methylcellulose, from about 40 wt. % to about 60 wt. % hydroxypropyl cellulose, and about 4 wt. % to about 12 wt. % tannic acid.

24. The pharmaceutical dosage form of claim 12, comprising from about 10 wt. % to about 20 wt. % hydroxypropyl methylcellulose, from about 45 wt. % to about 50 wt. % hydroxypropyl cellulose, and about 4 wt. % to about 6 wt. % tannic acid.

\* \* \* \* \*